United States Patent
Avdeef et al.

(10) Patent No.: US 6,569,686 B2
(45) Date of Patent: May 27, 2003

(54) MEASUREMENT OF SOLUBILITY-PH PROFILES

(75) Inventors: Alex Avdeef, Boston, MA (US); Konstantin L. Tsinman, Chelmsford, MA (US)

(73) Assignee: Pion, Inc., Woburn, MA (US)

( * ) Notice: Subject to any disclaimer, the term of this patent is extended or adjusted under 35 U.S.C. 154(b) by 127 days.

(21) Appl. No.: 09/769,570

(22) Filed: Jan. 25, 2001

(65) Prior Publication Data

US 2002/0004244 A1 Jan. 10, 2002

Related U.S. Application Data

(60) Provisional application No. 60/178,616, filed on Jan. 28, 2000.

(51) Int. Cl.[7] .............................................. G01N 21/75

(52) U.S. Cl. ...................... 436/166; 436/164; 436/171; 436/174; 436/179

(58) Field of Search ...................... 435/134; 422/82.05, 422/82.09, 82, 100–104, 62, 75; 436/163, 166, 171, 172, 164, 174, 179, 180

(56) References Cited

U.S. PATENT DOCUMENTS

| | | | | |
|---|---|---|---|---|
| 4,127,687 A | * | 11/1978 | Dupont | 106/18.32 |
| 4,906,580 A | | 3/1990 | Meserole | 436/56 |
| 5,192,509 A | | 3/1993 | Surjaatmadja et al. | 422/75 |
| 5,677,286 A | * | 10/1997 | Shull et al. | 514/25 |
| 5,750,678 A | * | 5/1998 | Bauer et al. | 435/134 |
| 6,004,822 A | * | 12/1999 | Li et al. | 422/100 |
| 6,271,038 B1 | * | 8/2001 | Liu et al. | 204/450 |

FOREIGN PATENT DOCUMENTS

WO   WO 99/13328   3/1999

OTHER PUBLICATIONS

V. Holba, "Solubility and Thermodynamic Functions of Transfer for $[cr(en)_2Cl_2].[Cr(C_6H_5NH_2)_2(NCS)_4]$ from Water to Water–Organic Mixed Solvents", Chem. Papers, 53(4):227–232 (1999).*

Lilibeth dlC. Coo, "Spectrophotometric Study of the Solubility and the Protolytic Properties of 1–(2–Pyridylazo)–2–Naphthol in Different Ethanol–Water Solutions", Analytica Chimica Acta, 360:153–159 (1998).*

*Solubility Behavior of Organic Compounds*, David J.W. Grant, wt al., Techniques of Chemistry, vol. XXI, Copyright © 1990 by John Wiley & Sons, Inc., (List continued on next page.)

*Primary Examiner*—T. Tung
*Assistant Examiner*—Yelena Gakh
(74) *Attorney, Agent, or Firm*—Weingarten, Schurgin, Gagnebin & Lebovici LLP

(57) ABSTRACT

This invention relates to a method for the determination of solubility of a compound and an analytical device for carrying out said method. The basic method involves determining solubility of a compound by measuring the UV spectrum of a reference solution of the compound, under conditions avoiding or suppressing precipitation, and comparing it to the UV spectrum of a saturated sample solution of the compound. Variations of the basic method include: (a) making reference solutions either by dilution of the sample solution to the point where precipitation is avoided, or making reference solutions by adding a water-miscible cosolvent to the sample solution so that precipitation is suppressed, and comparing the UV absorbances of the compound under reference conditions to the compound in a saturated solution, (b) determining the true aqueous solubility from the effect on the $pK_a$ that results from dissolving the compound in an aqueous solution containing some DMSO (typically 0.1–5% v/v), and (c) correcting concentrations determined from the UV absorbance values for impurities and other factors that might affect the shape of the sample absorbance curve taken of the saturated solution.

21 Claims, 14 Drawing Sheets

OTHER PUBLICATIONS

*Estimation of the Increase in Insoluble Drugs as a Function of Bile Salt Concentration*, Sabena D. Mithani, et al., Pharmaceutical Research, vol. 13, No. 1, 1996, pp. 163–167.

*Dissolution of Ionizable Water–Insoluble Drugs: The Combined Effect of pH and Surfactant*, Junichi Jinno, et al., Journal of Pharmaceutical Sciences, vol. 89, No. 2, Feb. 2000, pp. 268–274.

*pH–Solubility Profiles of Organic Carboxylic Acids and Their Salts*, Z.T, Chowhan, Journal of Pharmaceutical Sciences, vol. 67, No. 9, Sep. 1978, pp. 1257–1260.

*Investigation of drug self–association in aqueous soluton using calorimetry, and osmometry*, Chengyue Zhu, d et al., International Journal of Pharmaceutics 130 (1996), pp. 159–168.

*General treatment of pH solubility profiles of weak acids and bases II. Evaluation of thermodynamic parameters from the temperature dependence of solubility profiles applied to a zwitterionic compound*, William H. Streng, et al., International Journal of Pharmaceutics, 25 (1985), pp. 135–145.

*Combined Effect of Complexation and pH on Solubilization*, Ping Li, et al., Journal of Pharmaceutical Sciences, vol. 87, No. 12, Dec. 1998, pp. 1535–1537.

*Improving the odds–High Throughput Techniques in New Drug Selection*, Charmaine P. Quarterman et al., Pharmaceuticals Inc., Aston Molecules Ltd.

*Hydrophobic Ion Pairing: Altering the Solubility Properties of Biomolecules*, Jeffrey D. Meyer, et al., Pharmaceutical Research, vol. 15, No. 2, 1998, pp. 188–193.

*Physicochemical Properties of Prostaglandin $F_{2a}$ (Tromethamine Salt): Solubility Behavior, Surface Properties, and Ionization Constants*, T.J. Roseman, et al., Journal of Pharmaceutical Sciences, vol. 62, No. 10, Oct. 1973, pp. 1680–1685.

*A. High–Throughput Screening Method For The Determination Of Aqueous Drug Solubility Using Laser Nephelometry In Microtiter Plates*, Bevan CD, et al, vol. 72, Anal. Chem. (2000), 1781–1787.

*PH–Metric log p. 3. Glass Electrode Calibration in Methanol–Water*, Applied to $pK_a$ Determination of Water–Insoluble Substances, Alex Avdeef, et al., Analytical Chemistry, vol. 65, No. 1, Jan. 1993.

*pH–Metric Solubility. 2: Correlation Between the Acid–Base Titration and the Saturation Shake–Flask Solubility–pH Methods*, Alex Avdeef, t al., Pharmaceutical Research, vol. 17, No. 1, 2000, pp. 85–89.

*High–Throughput Measurement of Solubility Profiles*, Alex Avdeef, pION Inc., pp. 305–325, Pharmacokenetic Optimization in Drug Research.

*General Treatment of pH–Solubility Profiles of Week Acids and Bases and the Effects of Different Acids on the Solubility of a Weak Base*, William H. Streng, et al., Journal of Pharmaceutical Sciences, vol. 73, No. 12, Dec. 1984. Pp. 1679–1684.

*Accurate Measurements of the Concentration of Hydrogen Ions with a Glass Electrode: Calibrations Using the Prideaux and Other Universal Buffer Solutions and a Computer–Controlled Automatic Titrator*, Alex Avedeef, et al., Analytical Chemistry, vol. 5, No. 14, Dec. 1978, pp. 2137–2142.

*pH–metric Solubility.1. Solubility–pH Profiles from Bherrum Plots. Gibbs Buffer and $pK_a$ in the Solid State*, Alex Avdeef, Pharm. Pharmacol. Commun., 1998, pp. 165–178.

*PH–Metric LogP 10. Determination of Liposomal Membrane–Water Partition Coeficients of Ionizable Drugs*, Pharmaceutical Research, vol. 15, No. 2, 1998, A. Avdeef, et al., pp. 209–215.

*pSOL, pION sales literature.*

*Experimental and Computational Approachs to Estimate Solubility and Permeability in Drug Discovery and Development Settings*; Lipinski et al., Copyright © 1997, Elsevier SCience B.V.

\* cited by examiner

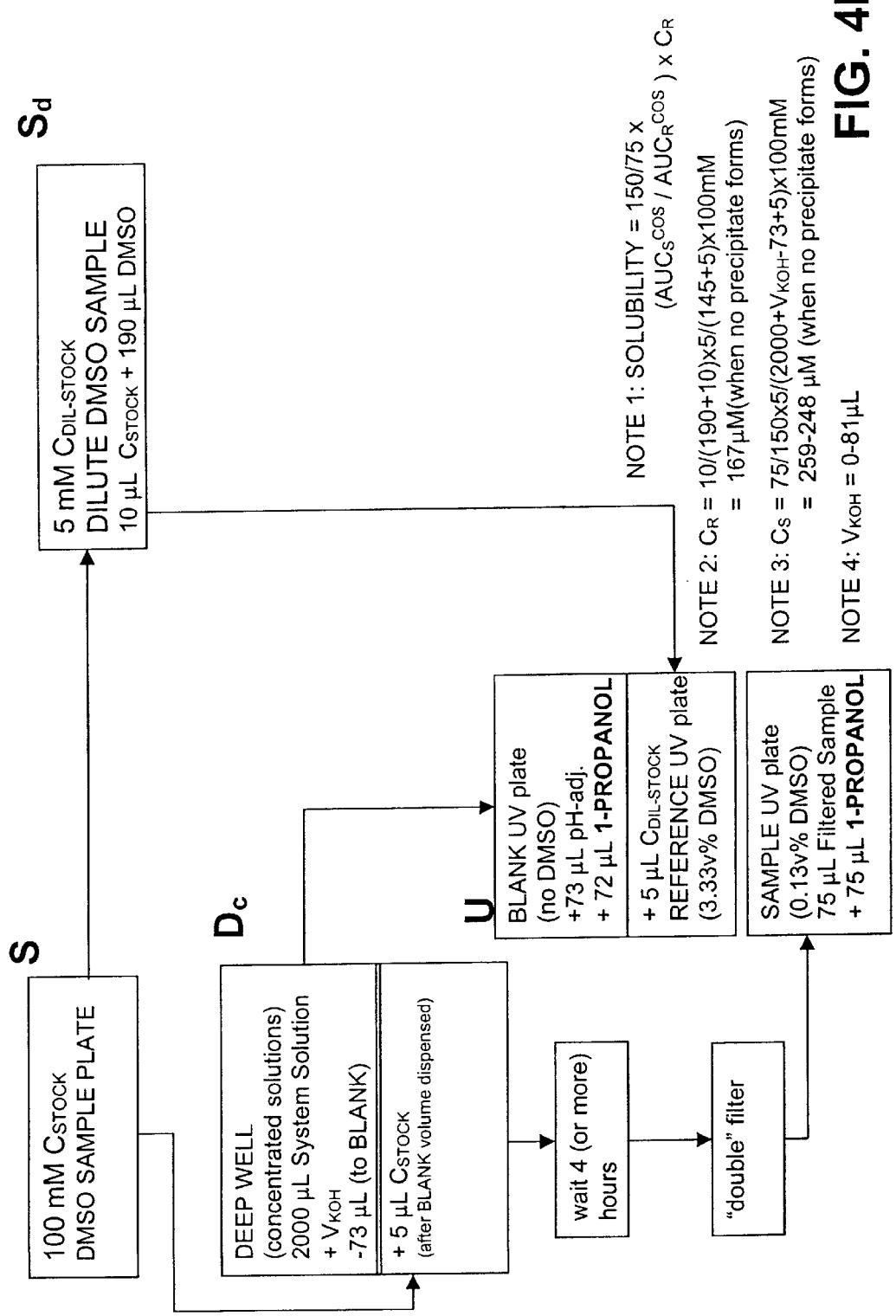

MEASUREMENT OF SOLUBILITY-PH PROFILES

CROSS REFERENCE TO RELATED APPLICATIONS

This application claims priority to U.S. Provisional Application No. 60/178,616 filed Jan. 28, 2000, which is incorporated in its entirety herein.

FIELD OF THE INVENTION

The measurement of aqueous solubility in a high-throughput screening environment plays an important role in the selection of the most promising drug candidate molecules in pharmaceutical research and development. The invention described involves a method, a simple, robust, high-throughput screen, that is applicable for the determination of the equilibrium solubility of sparingly soluble compounds and that may be used in pharmaceutical, biotechnology, and related industries. An analytical device has been designed to implement this solubility measurement technique.

BACKGROUND OF THE INVENTION

The 1990 treatise by Grant and Higuchi [D. J. W. Grant, T. Higuchi, Solubility Behavior of Organic Compounds, John Wiley & Sons: New York, 1990] comprehensively covers the known art. Many protocols have been described in the literature [S. Venkatesh, J. Li, Y. Xu, R. Vishnuvajjala, B. D. Anderson, i Pharm. Res. 1996, 13, 1453–1459; A. Avdeef, i Pharm. Pharmacol. Commun. 1998, 4, 165–178; A. Avdeef, C. M. Berger, C. Brownell, i Pharm. Res. 2000, 17, 85–89; A. Avdeef in B. Testa, H. van de Waterbeemd, G. Folkers, R. Guy (Eds.), *Lipophilicity in Drug Disposition: Practical and Computational Approaches to Molecular Properties Related to Drug Permeation, Absorption, Distribution, Metabolism and Excretion,* Univ. Lausanne, 2001, Ch. 22 (in press)] for measuring solubility-pH profiles, using various detection systems.

Classical approaches are based on the so-called saturation shake-flask method, and new rigorous methods are usually validated against it. However, most classical techniques are slow and cannot easily be adapted for the high-throughput needs of modern drug discovery research, one focus of our invention.

At the early stages of research, drug candidate compounds are stored as DMSO solutions, and solubility measurements need to be performed on samples introduced in DMSO, often as 10–30 mM solutions. It is well known that even small quantities of DMSO (<5%) in water can increase the solubility of molecules, and it is a challenge to determine the true aqueous solubility of compounds when DMSO is present, another focus of our invention.

Turbidimetric Ranking Assays

Turbidity detection-based methods, popularized by Lipinski and others [A. Lipinski, F. Lombardo, B. W. Dominy, P. J. Feeney, *Adv. Drug Deliv. Rev.* 1997, 23, 3–25; P. Q. Charmaine, M. B. Nicholas, A. K. Irwin, *Eur. Pharm. Rev.* 1998, 3(4); C. D. Bevan, R. S. Lloyd, *Anal. Chem.* 2000, 72, 1781–1787], in part have met some high-throughput needs of drug discovery research. The methods, although not thermodynamically rigorous, are an attempt to rank molecules according to expected solubilities. Various implementations of the basic method are practiced at several pharmaceutical companies, using custom-built equipment. Detection systems based on 96-well microtitre plate nephelometers have been introduced recently (e.g., Lab-Systems: Franklin, Mass., USA). The desirable automated solubility analytical device incorporating such a detector requires the operator to develop an appropriate chemistry procedure and to integrate a robotic fluidic system in a customized way. The shortcomings of the turbidity methodology are poor reproducibility (in part due to variability of scattering due to particle size, sometimes erratic scattering due to sedimentation of the sample suspension, and adhesion of suspensions to walls of vessels), the use of excessive amounts of DMSO, and from the view-point of the critical needs of the pharmaceutical industry, the lack of standardization of practice.

HPLC-Based Assays

Several pharmaceutical companies have taken the classical saturation shake-flask method and transferred it onto 96-well plate technology and a robotic liquid dispensing system, in an effort to increase throughput. Analyses are performed with reverse-phase HPLC. Often it is necessary to develop the appropriate chromatographic methods, since in discovery, compounds may not be sufficiently characterized at the early stages. However, generic fast gradient methods may be eliminating the need for method development. In some companies, the DMSO is first eliminated by a freeze-drying procedure, before the aqueous buffers are added, which adds significantly to the assay time and can be problematic with volatile samples. Chromatographic detection systems, although rich in information, being serial, are inherently slow. Data handling is often the rate-limiting step in the operations.

Ideal Solubility—pH Relationships

For ionizable molecules in dilute solutions (where salt precipitation may be ignored), when the log (logarithm) of the measured solubility is plotted vs. pH, the curve is bilinear, with one segment having a zero slope and the other segment having a unit slope (positive for acids and negative for bases). For example, for an acid such as diclofenac, the solubility is at a minimum for pH<3 (where the acid is largely uncharged), stays nearly constant (zero slope segment) as pH is increased, until it exceeds the $pK_a$ (3.99), after which the solubility increases by a decade for every increased unit of pH, as more and more of the compound converts from the uncharged state to the more-soluble negatively-charged state (unit slope segment). In a simple aqueous equilibrium system, the pH where the asymptotes of the horizontal and diagonal segments intersect is equal to the $pK_a$ of the solute. Under such ideal circumstances, it is possible to determine the $pK_a$ and the intrinsic aqueous solubility, $S_o$, of the compound from the crossing of the segments [Z. T. Chowhan, *J. Pharm. Sci.* 1978, 67, 1257–1260; W. H. Streng, H. G. H. Tan, *Int. J. Pharm.* 1985, 25, 135–145]. Such $pK_a$ values can be directly measured by commercially-available devices [C. D. Bevan, A. P. Hill, D. P. Reynolds, Patent Cooperation Treaty, WO 99/13328, Mar. 18, 1999; Sirius Analytical Instruments Ltd., UK].

Complications Which May Thwart the Reliable Measurement of Aqueous Solubility

Certain surface-active compounds when dissolved in water under conditions of saturation form self-associated aggregates or micelles, which can interfere with the determination of the true aqueous solubility and the $pK_a$ of the compound [T. J. Roseman, S. H. Yalkowsky, *J. Pharm. Sci.* 1973, 62, 1680–1685; C. Zhu, W. H. Streng, *Int. J. Pharm.* 1996, 130, 159–168]. When the compounds are very sparingly soluble in water, excipients are often added to enhance the rate of dissolution. However, the presence of the excipients also can interfere with the determination of the true aqueous solubility. If solubility measurements are done in the presence of simple surfactants [J. Jinno, D. -M. Oh, J. R. Crison, G. L. Amidon, *J. Pharm. Sci.* 2000, 89, 268–274], bile salts [S. D. Mithani, V. Bakatselou, C. N. TenHoor, J. B. Dressman, *Pharm. Res.* 1996, 13, 163–167], cyclodextrins [P. Li, S. E. Tabibi, S. H. Yalkowsky, *J. Pharm. Sci.* 1998, 87, 1535–1537], or ion-pair forming counterions [J. D. Meyer, M. C. Manning, *Pharm. Res.* 1998, 15, 188–193], extensive considerations need to be applied in attempting to extract the true aqueous solubility from the data, third focus of our invention.

BRIEF SUMMARY OF THE INVENTION

This invention relates to a method for the determination of solubility of a compound and an analytical device for carrying out said method. The basic method involves determining solubility of a compound by measuring the UV spectrum of a reference solution of the compound, under conditions avoiding or suppressing precipitation, and comparing it to the UV spectrum of a saturated sample solution of the compound. Variations of the basic method include: (a) making reference solutions either by dilution of the sample solution to the point where precipitation is avoided, or making reference solutions by adding a water-miscible cosolvent to the sample solution so that precipitation is suppressed, and comparing the UV absorbances of the compound under reference conditions to the compound in a saturated solution, (b) determining the true aqueous solubility from the effect on the $pK_a$ that results from dissolving the compound in an aqueous solution containing some DMSO (typically 0.1–5% v/v), and (c) correcting concentrations determined from the UV absorbance values for impurities and other factors that might affect the shape of the sample absorbance curve taken of the saturated solution.

Solubility determinations are illustrated with 15 sparingly-soluble generic, mostly-ionizable drugs (FIG. 1), covering about three orders of magnitude in solubilities, with the lowest value being about 0.1 µg/mL (terfenadine at high pH). The ionizable bases include amiloride, amitriptyline, chlorpromazine, miconazole, nortriptyline, phenazopyridine, propranolol, and terfenadine. The ionizable acid set consists of diclofenac, furosemide, indomethacin, 2-naphthoic acid, and probenecid. Piroxicam was picked as an example of an ampholyte, and griseofulvin as an example of a non-ionizable molecule. The results of the solubility measurements were compared to literature equilibrium solubility-pH values from reliable sources, and to values determined by the pSOL Model 3 (pION) acid-base titrator [A. Avdeef, C. M. Berger, C. Brownell, *Pharm . Res.* 2000, 17, 85–89].

BRIEF DESCRIPTION OF THE SEVERAL VIEWS OF THE DRAWING

FIG. 6 shows the expected ratios of the areas-under-the-curve, R (equation 5 below), corresponding to the examples in FIG. 5. Solubility values are derived under the conditions $0.05 < R < 1$ (equation 6). Note that 0.05 refers to the 20-fold dilution ratio in the aqueous dilution method.

FIG. 8 shows for several of the studied molecules the logarithm of the apparent solubility versus pH curves in solutions containing 0.5% (v/v) DMSO (solid line), and the corresponding calculated aqueous solubility versus pH, using equations from Table 1 below (dashed line). The circles represent measured points; the solid line represents the best-fit curve of the measured points, in accordance with the expected shape of a log S vs. pH curve; the dashed line represents the log S vs. pH curve after correction for the anomalies caused by DMSO, aggregation, and the like.

DETAILED DESCRIPTION OF THE INVENTION

Figure 1:
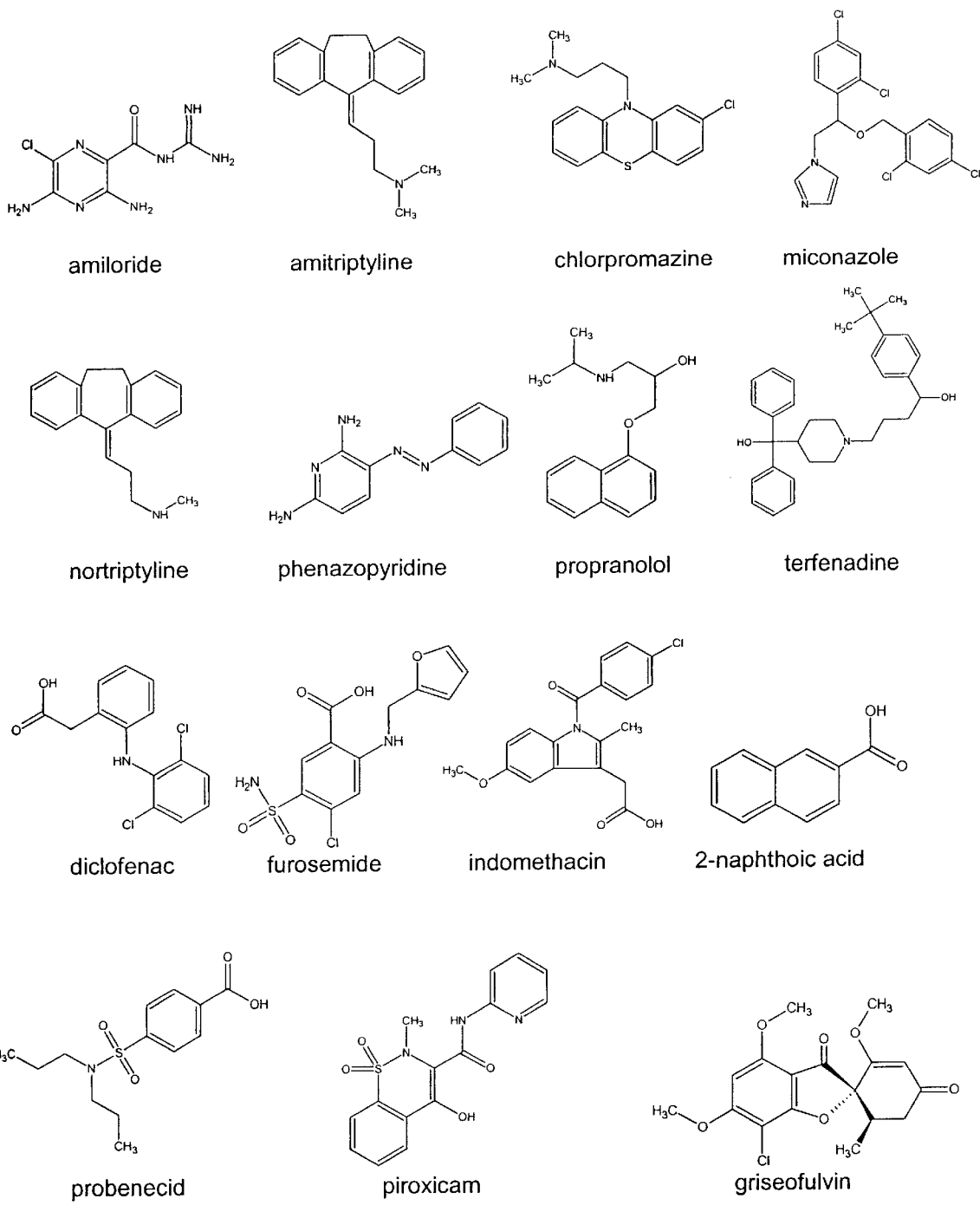
FIG. 1 shows the structure of compounds evaluated using the invention and for which data appears herein.

We have adapted the classical shake-flask method to the 96-well microtitre plate format, but our detection system is not based on the traditional, one-compound-at-a-time HPLC method. The invention is a parallel detection method, based on the use of a 96-well microtitre plate UV/visible (hence called 'UV') spectrophotometer. Our invention can measure 96 solubilities at a time, significantly increasing throughput. Compound-dependent method optimization is not required in the direct UV method.

(1) The essence of our invention is that of making concentration standards under conditions avoiding or suppressing precipitation for UV spectrophotometers (in two different implementations: (a) aqueous dilution and (b) cosolvent), using molecules, especially ionizable molecules, whose UV spectroscopic properties are unknown at the start of the assay. (Simply weighing the compounds and preparing solutions does not work in general, because the compounds precipitate under conditions necessary to characterize their solubilities.)

(2) Also, a novel and simple computational method is developed to extract the aqueous intrinsic solubilities of drug molecules from data altered by DMSO-drug binding, or drug-drug aggregation reactions, or drug reactions with non-ionizable excipients, using the difference between the apparent $pK_a$ measured by the analytical device and the true $pK_a$ measured by analytical devices available commercially (e.g., from Sirius Analytical Instruments Ltd., Forest Row, E. Sussex, UK).

(3) Also, an improved general method for determining concentration by UV spectrophotometry is derived, based on using a novel peak shape algorithm for adjusting weights in a whole-spectrum weighted regression analysis, matching spectra of reference solutions (of known concentration, under conditions avoiding or suppressing precipitation) to solutions containing analyte of unknown concentration (due to precipitation).

Definitions of Terms

If the molecule is ionizable, its charge depends on the pH of the solution in which it is dissolved. The pH at which the concentration of the charged form is equal to the concentration of the uncharged form is called the $pK_a$ of the molecule. For example, for the ionizable acid (or ionizable base), represented by HA (or B), chemists usually denote the equilibrium reaction by the equation $$HA \rightleftharpoons A^- + H^+ \text{ (or } BH^+ \rightleftharpoons B + H^+) \quad (1)$$

and the corresponding equilibrium ionization constant is defined as $$K_a = [A^-][H^+]/[HA] \text{ (or } K_a = [B][H^+]/[BH^+]) \quad (2)$$

By definition, $pK_a = -\log K_a$. When a solute molecule, HA (or B), is in equilibrium with its precipitated form, HA(s) (or B(s)), chemists usually denote the process by the equilibrium expression $$HA(s) \rightleftharpoons H \text{ (or } B(s) \rightleftharpoons B) \quad (3)$$

and the corresponding equilibrium constant is defined as $$S_o = [HA]/[HA(s)] = [HA] \text{ (or } S_o = [B]/[B(s)] = [B]) \quad (4)$$

By convention, $[HA(s)] = [B(s)] = 1$. Equations (3) represent the precipitation equilibria of the uncharged species, and are characterized by the intrinsic solubility equilibrium constant, $S_o$. (The zero subscript denotes the zero charge of the precipitating species.)

The values of the equilibrium constants in equations (2) and (4) depend on the solvent system used (water and aqueous buffers in our case), the inert salt used to adjust the ionic strength of the solution (e.g., NaCl or KCl), temperature (22–25° C. in our case), pressure (ambient in our case), and may be affected by organic components (other than the sample) in the aqueous solution, such as DMSO, propanol, surfactants, bile acids, lipophilic counterions, cyclodextrins, and the like. For example, if the solvent system were changed from water to 50% v/v methanol-water, then the $pK_a$s of acids would be higher and of bases would be lower, compared to values determined in pure water [A. Avdeef, J. E. A. Comer, S. J. Thomson, Anal. Chem. 1993, 65, 42–49].

We use the term solubility to mean the concentration of a solute (in units of moles per liter, M, or micrograms per milliliter, μg/mL) in a saturated pH-buffered aqueous solution. Under pH conditions where the sample molecule is essentially uncharged, the measured solubility is equal to the intrinsic solubility of the molecule. Solubility may depend on pH, but the intrinsic solubility, being a thermodynamic equilibrium constant, does not.

We will implicitly refer to $pK_a$s or log $S_o$ or log S of compounds as values determined in water or an aqueous buffer. When we use the term "apparent" $pK_a$, or "apparent" log $S_o$, we do so to emphasize that the aqueous value may not be evident when solutions contain components such as DMSO, propanol, surfactants, bile acids, lipophilic counterions, cyclodextrins, and the like, that may affect the ionization properties of the compound.

The term "stock" solution will refer to a solution made from a precisely known quantity of pure compound dissolved in a known volume of solvent, usually pure DMSO, usually at a 10–100 mM concentration level. Compounds are expected to be fully dissolved in the stock solution.

We use the term "reference" solution to mean a solution of the sample compound where the concentration of said compound is known. The reference solution can be prepared by precisely weighing a quantity of the pure compound and dissolving it in a precise volume of solvent (usually water or aqueous buffer), or by adding a precise volume of a stock solution of said compound to a precise volume of solvent, under conditions avoiding or suppressing precipitation. Two ways are developed to suppress or avoid precipitation: (a) simply make a dilute aqueous solution, below the limit of solubility, or (b) add water-miscible cosolvent to an otherwise saturated aqueous solution.

The term "saturated" solution refers to a solution at equilibrium, containing enough sample compound, so that a portion of the compound is precipitated out of the solution and a portion remains dissolved, at a concentration equal to the solubility. In other words, a saturated solution of a compound contains an excess of undissolved solid form of the compound in contact with its solution.

The term "supersaturated" solution refers to a solution containing no solid and more dissolved compound than expected from its equilibrium solubility. Usually, such solutions are unstable, and given enough time, will precipitate.

By the term "filtration", we broadly mean the separation of the precipitated solid from a saturated solution, either by passing said solution through a filter, by sedimentation, by centrifugation, or by any other separation means.

Saturated solutions are usually "concentrated," and reference solutions are usually "dilute," unless cosolvent is used.

To cause the formation of a saturated solution, a small aliquot of the stock solution (typically 1–50 μL) or a weighed quantity of compound is added to an aqueous buffer solution (typically 1000–2000 μL), which is called the "system solution" here.

By the term "excipient", we mean any additive in a solution that may affect the solubility of the solute. More specifically, we mean a non-ionizable additive in the pH interval where the sample compound is ionizable. Examples of such additives, as we use the term, are DMSO, surfactants, bile salts, phospholipids, cyclodextrins, ion-pair forming counterions, polymers, cosolvents, and combinations thereof.

Components of the Analytical Device of the Invention

Hardware

Figure 2:
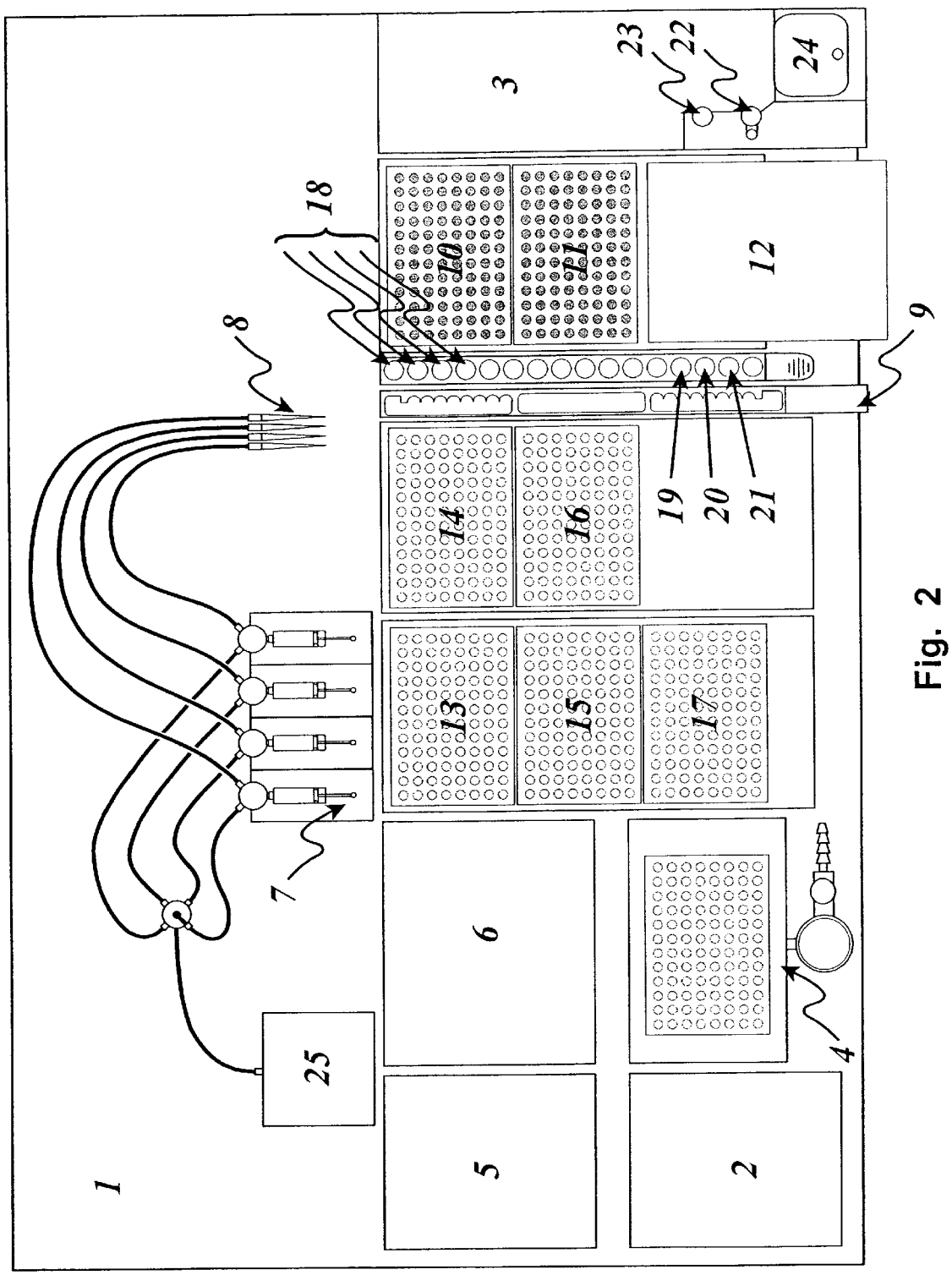
FIG. 2 represents a schematic of an analytical device utilized to carry out the methods described in this patent.

The analytical device, shown in a block diagram in FIG. 2, consists of a robotic liquid handling system (1), a microtitre plate scanning UV spectrophotometer (2), a pH titrator device (3), a microtitre plate vacuum filtration manifold (4), a microtitre plate washer (5), a microtitre plate orbital shaker (6), four precision syringe dispensers (7), four dispenser arms positioned by the robot anywhere on the worktable of the liquid handling system (8), a wash station and waste trough (9), a small-tips pipet rack holder (10), a large-tips pipet rack holder (11), a used-tip collector (12), a stock sample microtitre plate (13), a 20-fold diluted stock sample microtitre plate (14), a deep-well microtitre plate for saturated solutions (15), a deep-well microtitre plate for reference solutions in the aqueous dilution method (16), a plastic UV microtitre plate (17), four test tubes filled with rinse solution (18), a test tube for cosolvent (19), a test tube for the DMSO (20), a test tube for 0.5 M KOH titrant (21), a titration vessel, with a magnetic stir bar and a magnetic stir motor underneath (22), a test tube to store the pH electrode (23), and an electrode wash station (24).

The robotic liquid handling system (1), is equipped with four high-precision 0.5 mL syringes equipped with two-way valves (7), and four dispenser arms, with conductive-plastic disposable tips (8), a liquid-level sensing system, two racks for tips (10,11), six microtitre plate holders (13–17), dram-size vial and test tube holders (18–21), a rinse and waste station (9), and approximately 100×50 cm workspace (e.g., Genesis 100/4 System from Tecan, Research Triangle Park, N.C., USA).

A 96-well microtitre plate scanning spectrophotometer is a part of the analytical device (2), with wavelength range at least 200–850 nm, with <5 nm resolution (e.g., SpectraMAX 190 from Molecular Devices, Sunnyvale, Calif., USA).

Although the 96-well microtitre plate format is used preferentially, the method and the analytical device can be constructed with other plate formats, for example, the 384-well microtitre plate format.

Although our preferred detector system is a scanning microtitre plate UV spectrophotometer, diode-array microtitre plate UV spectrophotometers, and flow-through UV detector systems, scanning or diode array, may also be used.

Although a UV detector is the preferred embodiment of the invention, the detector may be any suitable spectrophotometric analytical detector, such as ultraviolet or visible spectrophotometer, a fluorimeter, a colorimeter, a light-scattering device, polarimeter, optical rotation or circular dichroism detector.

A pH titrator (3) is used, having a vessel to hold the solution being titrated (22), equipped with a pH meter capable of precisely reading pH from 1.5–12.5, having a dispenser able to add 0.5 M KOH titrant in precise small amounts, such as 1 $\mu$L (7), and able to stir the solution during titrant additions (e.g., pSOL Model 3 from pION, Woburn, Mass., USA).

A vacuum filtration manifold (e.g., from Whatman) for microtitre plates (4) is used, with a source of vacuum.

A microtitre plate washer (5) is used, with a 75% v/v methanol wash solution (e.g., from Tecan).

A microtitre plate orbital shaker is used (6) (e.g., from Lab-Line Instruments, Inc.).

Also used are commercially-sourced 96-well polyethylene/polypropylene microtitre plates, in 0.4 and 2.2 mL well capacities (numerous sources); commercially-source plastic UV plates (e.g., from Corning-Costar or Greiner).

In the basic protocols described below, 8 compounds are sampled in each microtitre plate, at 12 different pH-buffer solutions. This reflects the 8-row×12-column layout of the microtitre plates. The procedures can be easily scaled up three-fold to 24 samples per day on the present robotic system, still preserving the 12-pH profile, or to 384 samples per day at one pH.

Reagents

A universal buffer system solution is used (25), designed to have a linear response to alkali titrant additions in the pH range 3–10, with nonlinearity in pH of about ±0.05 pH units. The solution possesses buffer components with low-UV absorption (each component with OD<0.05 at 220 nm for a 4.5 mm path length). The solution possesses buffer components with low tendency to interact with sample species, and specifically excludes phosphate and citrate. A 2-L solution of the buffer, the pH of which is initially near 3, has the capacity of about 100 mL of 0.5 M KOH when pH is raised to 10. The ionic strength of the universal buffer solution is about 0.01 M. Such a universal buffer solution is specifically designed for solubility measurements and is commercially available from pION.

A standardized 0.5 M KOH solution is used (21), containing <0.5% M/M carbonate (available from a number of commercial sources).

Organic solvents are used: spectroscopic grade (or better) DMSO (20) and 1-propanol (19) (numerous commercial sources).

Software

A computer program is used, which controls the actions of the robotic fluidic delivery system, prompts the operator to perform certain tasks, controls the actions of the spectrophotometer, and processes the spectral data to determine aqueous solubilities as a function of pH and the intrinsic aqueous solubility, displays the data graphically and in report forms, and which transfers the results of the analyses to a Microsoft® Excel spreadsheet. It is commercially available from pION.

The software is loaded on a Windows NT® computer, which connects to the robotic workstation (1), the UV spectrophotometer (2), and the pH titration device (3), by RS232 serial cables, and controls the actions of the analytical device and stores the spectra collected for further processing.

Implementation Based on Aqueous Dilution Method

Figures 3A, 4A:
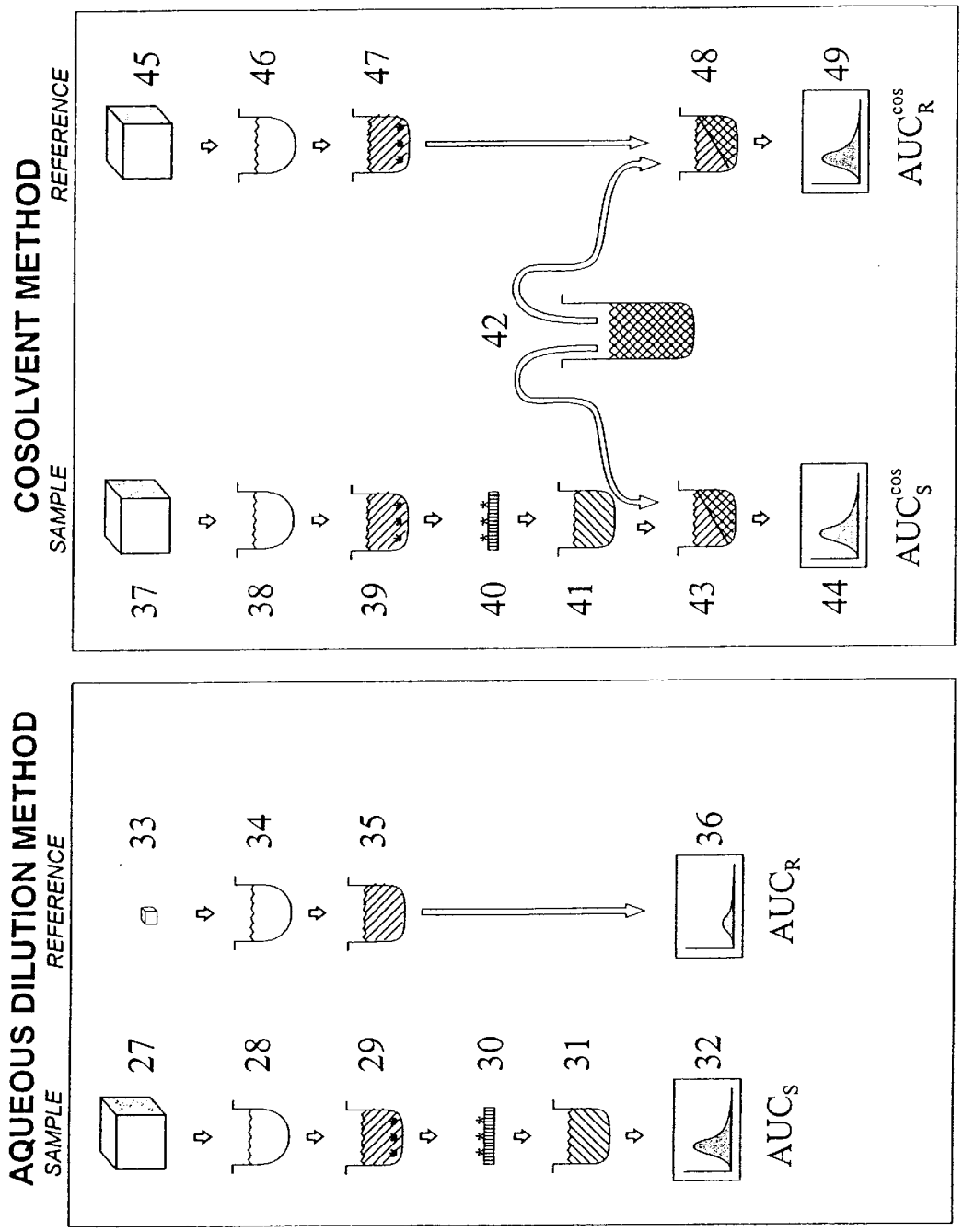
FIG. 3 is a flow chart showing the aqueous dilution method: (a) general depiction, (b) specific implementation.
FIG. 4 is a flow chart showing the cosolvent method: (a) general depiction, (b) specific implementation.

The diagram in FIG. 3a shows the general concept of the aqueous dilution method of preparing reference solutions for UV measurements. The "sample" track on the left side of FIG. 3a depicts a series of steps leading up to the taking of the sample spectrum. A known quantity of sample (27) is added to a known volume of the universal buffer solution of known pH (28), the amount of said sample being sufficient to cause precipitation to occur in the formed saturated solution (29). After waiting a period of time to allow the saturated solution to reach a desired steady state, the solution is filtered (30) to remove the solid, to obtain a clear solution (31), whose spectrum is then taken by the UV spectrophotometer (32). The mathematical treatment of the spectral data (described below) yields the area-under-the-curve of the filtered sample solution (31), $AUC_S$.

The "reference" track on the right side of FIG. 3a depicts a series of steps leading up to the taking of the reference spectrum. A known quantity of sample (33) is dissolved in a known volume of the universal buffer solution of known pH (34), the amount of said sample being X-times less than 27, in order to avoid precipitation in the formed solution (35). The spectrum is immediately taken by the UV spectrophotometer (36), to take advantage of the possibility that solution 35 may be "supersaturated" (that is, solid should have precipitated, but because not enough time was allowed for the solid to precipitate, the solution was temporarily clear and free of solid). The mathematical treatment of the spectral data yields the area-under-the-curve of the reference sample solution (35), $AUC_R$.

When the ratio of the two AUC values, $$R = AUC_R/AUC_S \quad (5)$$

is greater than 1, supersaturation is indicated, and solubility can be determined by equation (6) below.

When R=1, the sample and the reference solutions are both saturated, and solubility cannot be determined, unless visual inspection of solution 35 indicates that no solid is present, which could happen in a supersaturated solution. In this case, solubility can be determined by equation (6) below.

To overcome the situation of R=1 with both solutions being saturated, a higher value of X needs to be tried, and the procedure repeated until R<1.

If solubility cannot be determined because R=1, one can conclude that the solubility is less than or equal to the calculated concentration of 35 (the calculation ignoring precipitation).

At the other end of the scale of ratios, when R=1/X, the compound is fully dissolved in both the pre-filtered sample solution (29) and the reference solution (35), and solubility cannot be determined. (Ideally, R cannot be less than 1/X, unless Beer's law is violated.) However, one can conclude that solubility is greater than or equal to the calculated concentration of the solution 35 (concentration $C_R$). To overcome this particular limitation, more sample 27 may be used.

When the condition 1/X<R<1 is met, then the solubility of the sample compound is $$S = C_R/R \quad (6)$$

where $C_R$ is the calculated concentration of 35.

In example 1, we implement the aqueous dilution method with the value of X=20.

Implementation Based on Cosolvent Method

The diagram in FIG. 4a shows the general concept of the cosolvent method of preparing reference solutions for UV measurements. The "sample" track on the left side of FIG. 4a depicts a series of steps leading up to the taking of the sample spectrum in a water-cosolvent solution. A known quantity of sample (37) is added in a known volume of the universal buffer solution of known pH (38), the amount of said sample being sufficient to cause precipitation to occur in the formed saturated solution (39). After waiting a period of time to allow the saturated solution to reach a desired steady state, the solution is filtered (40) to remove the solid, and obtain a clear solution (41).

A volume Y of a water-miscible cosolvent 42 is added to a volume Z of solution 41 to produce a new solution 43, in which the compound is diluted by Z/(Y+Z), from its concentration in solution 41. The spectrum of solution 43 is then immediately taken by the UV spectrophotometer (44), to minimize evaporation of the water-cosolvent solution. The mathematical treatment of the spectral data yields the area-under-the-curve of the filtered cosolvent sample solution (43), $AUC_S^{COS}$.

Suitable cosolvents may be selected from a number of water-miscible organic solvents, such as acetonitrile, methanol, ethanol, iso-propanol, 1-propanol, ethylene glycol, propylene glycol, polyethylene glycol 400 (PEG-400), 1,4-dioxane, dimethylformamide, acetone, tetrahydrofuran, dimethyl-sulfoxide (DMSO), and mixtures thereof. The ones with the lowest vapor pressure, the greatest capability in dissolving a solute (i.e., highest solubilizing power), and the lowest UV absorption are preferred.

The "reference" track on the right side of FIG. 4a depicts a series of steps leading up to the taking of the reference spectrum in a water-cosolvent solution. A known quantity of sample (45) is added to a known volume of the universal buffer solution of known pH (46), the amount of said sample being comparable to that of 37, no effort being made in this step to suppress precipitation in the formed solution (47).

A volume Y of a water-miscible cosolvent 42 is added to a volume Z of solution 47 to produce a new solution 48, in which the compound is diluted by Z/(Y+Z), from its concentration in solution 47.

It is necessary to ensure that the cosolvent completely dissolves the compound in solution 48. If this is not the case, different values of Y and/or Z must be chosen and the whole procedure repeated to ensure that solution 48 is solid-free.

The spectrum of solution 48 is then immediately taken by the UV spectrophotometer (49), to minimize evaporation of the water-cosolvent solution. The mathematical treatment of the spectral data yields the area-under-the-curve of the filtered cosolvent sample solution (48), $AUC_R^{COS}$.

Define the ratio of the two AUC values, $$R^{COS} = AUC_R^{COS}/AUC_S^{COS} \quad (7)$$

The solubility of the sample compound is $$S = (1+Y/Z)C_R^{COS}/R^{COS} \quad (8)$$

where $C_R^{COS}$ is the calculated concentration of the compound in solution 48.

In example 2, we implement the cosolvent method with the value of Z/(Z+Y)=0.5, using 1-propanol.

Figure 7:
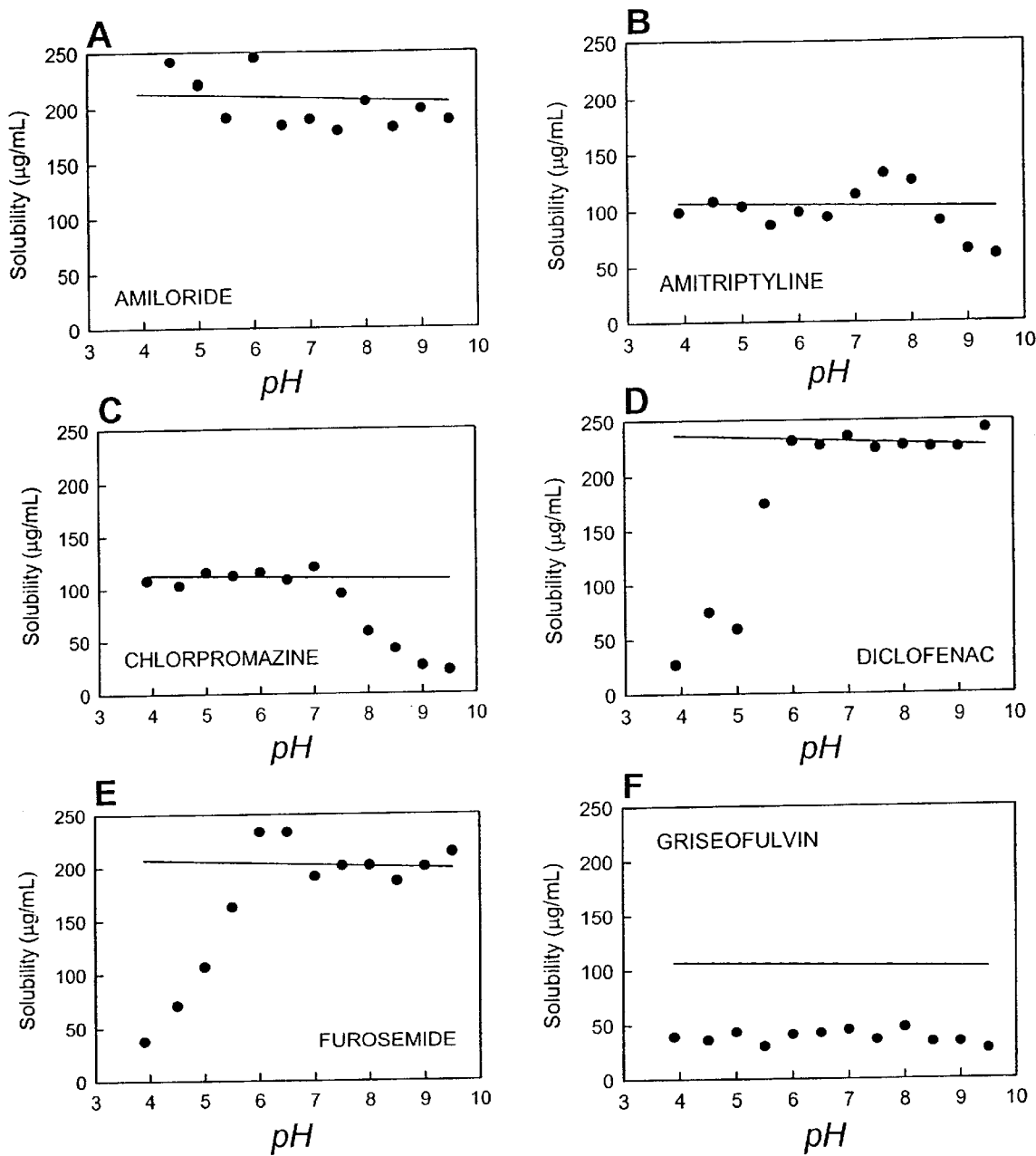
FIG. 7 shows curves generated from data, using equation 6, for solubility as a function of pH for several of the compounds studied by the aqueous dilution method. The horizontal lines represent the maximum possible sample concentration, $C_s$. The sample solution is not saturated when the discrete points coincide with the horizontal line, indicating that the solubility cannot be determined for those points.
Figure 8:
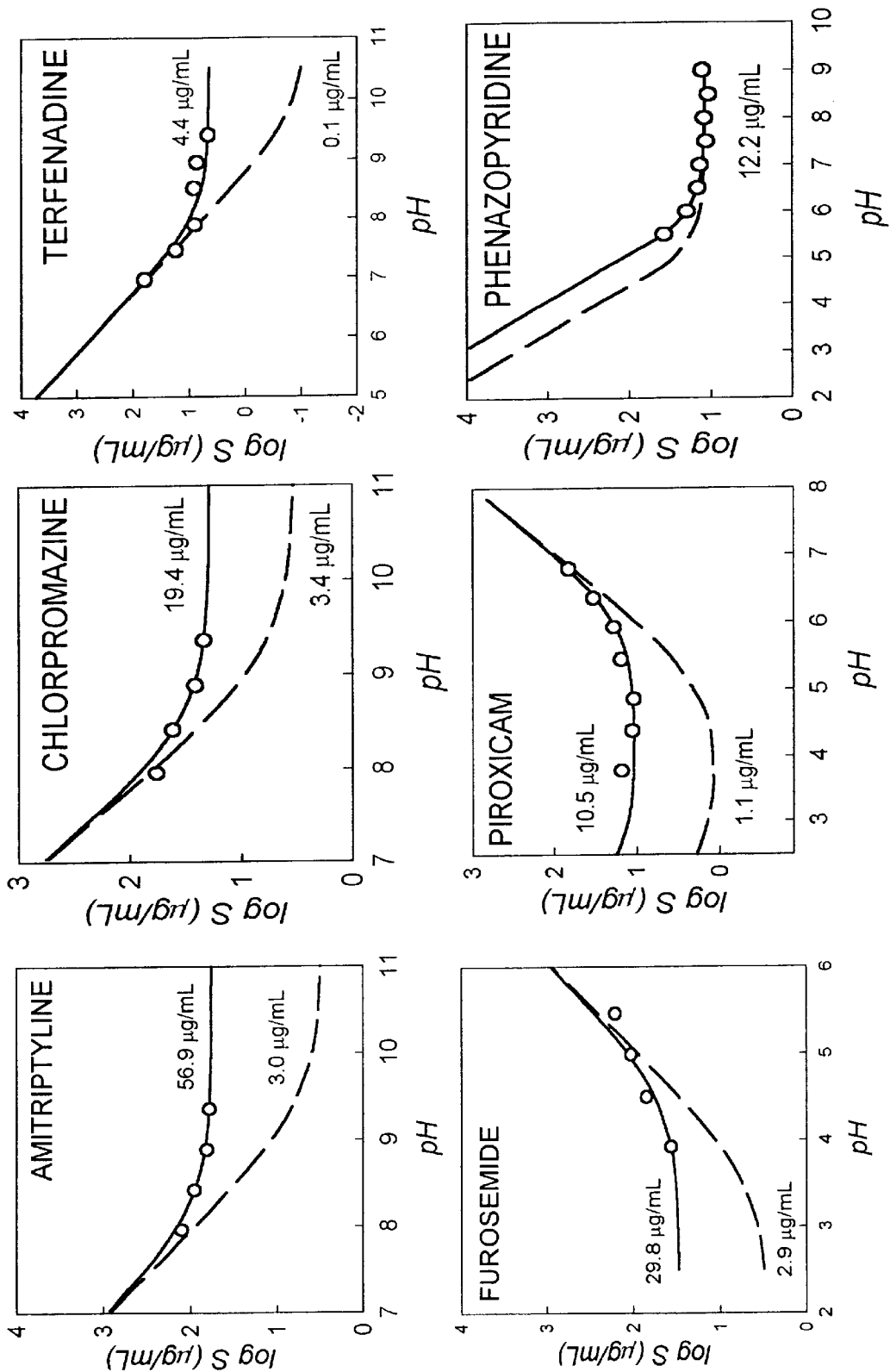

Method Using $pK_a$-Shifts for Determining True Aqueous Solubility of Ionizable Compounds in the Presence of Non-Ionizable Chemicals that Distort the Solubility-pH Profiles DMSO Binding to the Uncharged Form of a Compound Although the results depicted in FIG. 7 (plots of experimental S vs. pH) were very satisfactory at first sight, we soon discovered unexpected anomalies, which are not immediately apparent from the figures. The aberrations became evident when log S were plotted vs. pH (FIG. 8).

We found that the log S vs. pH curves (cf., Background section) were altered in the presence of 0.5% v/v DMSO, in that the apparent $pK_a$ values, $pK_a^{APP}$, derived from log S vs. pH, were different from the true $pK_a$ values by about one log unit. The $pK_a^{APP}$ values were generally higher than the true $pK_a$s for ionizable acids ("positive" shift), and lower than the true $pK_a$s for ionizable bases ("negative" shift).

We believe that this is caused by DMSO binding to the drugs. Although we did not anticipate it at first, we actually had collected the data necessary to calculate the extent of drug—DMSO binding, and also to correct for the effect, to obtain true aqueous solubility -pH profiles. For example, equation (9) represents the binding of the uncharged species by n molecules of DMSO (e.g., in 0.5% v/v).

$$HA + n\ DMSO \rightleftharpoons HA(DMSO)_n \quad (9)$$

If the effect of the DMSO is present, and it is ignored in the analysis, then the determined solubility is not the value one would measure in the absence of DMSO.

We discovered that if one determines the $pK_a^{APP}$ (in the presence of the DMSO effect) in the solubility assay, and subtracts from it the true $pK_a$ (determined using commercial instruments such as those from Sirius, UK), the difference, when subtracted from the logarithm of the apparent (DMSO-distorted) solubility, $S_o^{APP}$, yields the true aqueous solubility constant:

$$\log S_o = \log S_o^{APP} - (pK_a^{APP} - pK_a), \text{ for ionizable acids} \quad (10)$$

DMSO makes the compound appear more soluble, and the true aqueous solubility can be determined from the apparent solubility by subtracting the $pK_a$ difference, as done in equation (10).

Furthermore, we discovered that if one is considering the case of an ionizable base, such as chlorpromazine, the shift of the $pK_a$ is to values lower than the true $pK_a$. The corrective treatment is indicated by equation (11)

$$\log S_o = \log S_o^{APP} + (pK_a^{APP} - pK_a), \text{ for ionizable bases} \quad (11)$$

For an amphoteric molecule (which has both acid and base functionality) with two $pK_a$s, either equation (10) or equation (11) may be used, depending on which of the two $pK_a$s is selected.

FIG. 8 illustrates the apparent solubility -pH curve (solid line) and the true aqueous solubility-pH curve (dashed line), correcting for the effect of DMSO for several of the molecules considered.

Uncharged Forms of Compound-Compound Aggregation

Shifts in the $pK_a$ can also be expected if water-soluble aggregates form from the uncharged monomers. This may be expected with surface active molecules or molecules such as piroxicam [J. Jinno, D. -M. Oh, J. R. Crison, G. L. Amidon, *J. Pharm. Sci.* 2000, 89, 268–274]. Consider the case where no DMSO is present, but aggregates form, of the sort

$$m\, HA \rightleftharpoons (HA)_m \quad (12)$$

The assumption is that the aggregates are water soluble, that they effectively make the compound appear more soluble, and if ignored, they will lead to the erroneous assessment of solubility. We discovered that equations (10) or (11), for ionizable acids or ionizable bases, respectively, applies also to the case of aggregation.

Compound-Compound Aggregation of Charged Ionizable Bases

Consider the case of an ionizable base, where the protonated, positively charged form self-associates to form aggregates, but the uncharged form does not. We may have this case with phenazopyridine (FIG. 8). Phenazopyridine is a base which consistently shows positive shifts in its apparent $pK_a$, the opposite of what's expected of uncharged-compound DMSO/aggregation effects. A rationalization of this effect can be based on the formation of partially protonated aggregates (perhaps micelles) For example, one can hypothesize that one of the species is $(BH^+)_n$.

$$n\, BH^+ \rightleftharpoons (BH^+)_n \quad (13)$$

We discovered that for such a case, the observed solubility-pH curve is shifted horizontally (not vertically, as with uncharged-compound DMSO/aggregation effects), and that the apparent intrinsic solubility is not affected by the phenomenon.

Compound-Compound Aggregation of Charge Ionizable Acids

Consider the case of an ionizable acid, where the de-protonated, negatively-charged form, is strongly self-associated, but the uncharged form is not. We may have this case with prostaglandin F2α [T. J. Roseman, S. H. Yalkowsky, *J. Pharm. Sci.* 1973, 62, 1680–1685]. Prostaglandin is an ionizable acid with a reported negative shift in its apparent $pK_a$, the opposite of what's expected of uncharged-compound DMSO/aggregation effects. A rationalization of this effect can be based on the formation of partially deprotonated aggregated complexes (perhaps micelles). One can hypothesize a reaction similar to equation (12), but involving negatively-charged ions. The reported solubility-pH curve is shifted horizontally (not vertically, as with uncharged-compound DMSO/aggregation effects), and that the apparent intrinsic solubility is not affected by the phenomenon.

Ionizable Compound Binding by Non-ionizable Excipients

We have concluded that a number of phenomena, similar to those of reactions (9), (12), and (13), will shift the apparent $pK_a$ in a manner of the above discussions. For example, the additives in drug formulations, such as surfactants, bile salts, phospholipids, ion-pair forming counterions, cyclodextrins or polymers may make the drug molecule appear more soluble. As long as such excipients do not undergo a change of charge state in the pH interval of interest (i.e., the excipients are effectively non-ionizable), and the drug molecule is ionizable in the pH interval of interest, the difference between the apparent $pK_a$ and the true $pK_a$ will reveal the true aqueous solubility, as if the excipient were not present.

Table 1 summarizes some of the relationships developed between solubility, $pK_a$, and $pK_a^{APP}$.

TABLE 1

True Aqueous Solubility Determined from $pK_a$ Shifts of Monoprotic Compounds

| Ionizable Compound Type | $\Delta = pK_a^{APP} - pK_a$ | true aqueous log $S_o$ | Examples (from FIG. 8 and literature) |
|---|---|---|---|
| acid | $\Delta > 0$ | log $S_o^{APP} - \Delta$ | diclofenac, furosemide, indomethacin, probenecid, naphthoic acid |
| acid | $\Delta <$ or $= 0$ | log $S_o^{APP}$ | prostaglandin F2α[a] |
| base | $\Delta >$ or $= 0$ | log $S_o^{APP}$ | phenazopyridine |
| base | $\Delta < 0$ | log $S_o^{APP} + \Delta$ | amitriptyline, chlorpromazine, miconazole, terfenadine |

[a]T. J. Roseman, S. H. Yalkowsky, J. Pharm. Sci. 1973, 62, 1680–1685.

Area-Under-the-Curves (AUC) Determined by Weighted Regression Method

The method utilized by the analytical device for determining concentrations of species by UV spectroscopy is based on a weighted regression analysis of whole spectra. All the 65–130 measured absorbances from each microtitre plate well may be used in the analysis. The concentration of the reference species is known, and the object of the analysis is to assess the unknown concentration of the sample in the filtered solution, by applying Beer's law.

The calculated absorbance of the sample species at a particular wavelength i, $a_i^{calc}$, can be related to the absorbance values of the reference species, $a_i^{REF}$, the absorbance of DMSO (scaled to the units of the DMSO concentration in the reference well), $a_i^{DMSO(REF)}$, and the absorbance of the sample solution "blank" (buffers and the plastic microtitre plate), $a_i^{BLK(SAMPLE)}$:

$$a_i^{calc} = p_0 a_i^{REF} + p_1 a_i^{DMSO(REF)} + p_2 a_i^{BLK(SAMPLE)} \quad (14)$$

where $p_0$, $p_1$, and $p_2$ are unknown parameters. In turn, the absorbance of the reference species is derived from the observed reference spectrum, corrected for DMSO and blank:

$$a_i^{REF} = a_i^{REF(TOTAL)} - a_i^{DMSO(REF)} - a_i^{BLK(REF)} \quad (15)$$

The 'reference' spectrum is that of the compound of known concentration, and the 'sample' spectrum is that of the same compound, but of unknown concentration. At each desired wavelength i, the value of $a_i^{DMSO(REF)}$ is independently established: the DMSO absorbance curve is characterized from measurements of solutions containing all components except for the sample species. The 'blank' absorbances are measured before each assay, by sampling the microtitre plate filled only with the universal buffer solution. So, $a_i^{BLK(REF)}$ and $a_i^{BLK(SAMPLE)}$ are then known.

The object of the analysis is to determine the three unknown parameters $p_0$, $p_1$, and $p_2$ (The parameter $p_0$ is used directly in solubility determination; usually the other two parameters are determined to have near unit values.) This is done by weighted linear regression analysis [P. R. Bevington, "Data Reduction and Error Analysis for the Physical Sciences," McGraw-Hill: New York, 1969, pp. 164–186], as outlined below.

Define a column-vector of the unknown parameters, $p=(p_0, p_1, p_2)$. Define a row-vector, $b_i$, at each wavelength i, consisting of the three independent parameters $a_i^{REF}$, $a_i^{DMSO(REF)}$, and $a_i^{BLK(SAMPLE)}$, $$b_i = (a_i^{REF}, a_i^{DMSO(REF)}, a_i^{BLK(SAMPLE)}) \quad (16)$$

so that equation (14) may be expressed in vector notation as $$a_i^{calc} = b_i p \quad (17)$$

For all the measured wavelengths (typically, i=0 to N−1, where N=number of wavelengths measured), equation (17) may be expressed in an matrix notation, $$a^{calc} = Bp \quad (18)$$

Without the subscript, $a^{calc}$ denotes the column-vector of N rows (the number of discrete wavelengths measured), and B denotes the N-rows×3-columns matrix composed of the N individual $b_i$ vectors.

The parameters p are determined by finding a solution which minimizes the sum of weighted residuals $$Q = \sum_{i=0...N-1} (a_i^{obs} - a_i^{calc})^2 / \sigma_i^2 \quad (19)$$
$$= a^{obs,T} W a^{obs} - p^T B^T W a^{obs} - a^{obs,T} WBp + p^T B^T W B p$$

where $a_i^{obs}$ is the measured absorbance of the sample at wavelength (dependent variable), $\sigma_i^2$ is the estimated variance in the measured dependent variables $a_i^{obs}$, T is the transpose operator, and W is the diagonal matrix of weights, each $i^{th}$ element being the inverse variance, $1/\sigma_i^2$. The model equation, $a_i^{calc}$, is a function of the three p parameters, as well as the independent variables, $\lambda_i$ ($i^{th}$ wavelength) and $b_i$.

The elements of p are determined by setting the derivative of Q with respect to $p^T$ to zero and solving for p.

$$p = (B^T WB)^{-1} (B^T W a^{obs}) \quad (20)$$

Note that $p_0$ may be substituted into equations (5) and (7) as, $$p_0 = AUC_S / AUC_R \quad (21)$$

Weighting Scheme Based on Peak Shape Anomalies

The method utilized by the analytical device for determining concentrations of species by UV spectroscopy is based on a weighted regression analysis of whole spectra, as described in the last section. The technique is unique in how it assigns weights to the data, to make the assessment of concentrations more reliable, especially when samples are not entirely pure.

The normal weighting scheme used in equation (19) is constructed from the variances $$\sigma^2(a) = \sigma_c^2 + (\sigma_\lambda da/d\lambda)^2 \quad (22)$$

In the software of the analytical device, $\sigma_c=0.0002$ (absorbance units), the fixed contribution to the variance in the measured absorbance (experimentally determined by replicate baseline measurements, usually in the domain 450–500 nm), and $\sigma_\lambda=0.2$ nm (estimated error in wavelength, specified by the UV spectrophotometer manufacturer). The dependent variables, $a_i^{obs}$, and the independent variables, $\lambda_i$, are all assumed to be subject to error. The weighting scheme properly recognizes that measurements of absorbance on the steep sides of peaks are not as reliable as those near the peak top or from the baseline portions.

However, suppose that the sample spectrum has an "impurity" absorption (or scattering due to dust particles) at a particular wavelength, which is not found in the reference spectrum. If the impurity portion in the sample spectrum were not treated in any special way, then the procedure of the previous section would overestimate $p_0$, due to the added contribution of the impurity absorbance.

Consider a sample solution containing a mixture of components (i.e., impurities). The observed spectrum would be a manifold of several contributing spectra. It is reasonable to assume that the solubilities of all the components are different. If a saturated solution is made of the mixture, some components will precipitate and some will not. The consequence of this is that the UV spectrum of the manifold may change in shape as a result of the precipitation. The shape-based weighting scheme can detect such anomalies, minimizing their effect on the p-parameter determination.

The calculation scheme assesses the peak maximum, $a_{max}^{REF}$, and the wavelength, $\lambda_{max}$, at which the maximum occurs for the reference spectra. For any given wavelength i, the following reference and sample ratios are calculated:

$$r_i^{REF} = a_i^{REF} / a_{max}^{REF} \quad (23)$$

$$r_i^{SAMPLE} = a_i^{SAMPLE} / a_{max}^{SAMPLE} \quad (24)$$

where $a_{max}^{SAMPLE}$ is the sample absorbance at $\lambda_{max}$. If the peak in the sample had the identical shape as the peak in the reference solution, then the two ratios, (23) and (24) would be the same. However, if it happens that the impurity absorbance is at its maximum at the particular wavelength i, then the reference ratio would be greater than the sample ratio. Define a constant that is the ratio of the two above ratios:

$$s_i = |r_i^{SAMPLE} / r_i^{REF}| \quad (25)$$

Furthermore, define the empirically-optimized scale factor $k_i$:

$$k_i = 10^{+6.3(s-1)} \text{ for } s_i > 1 \quad (26a)$$

or $$= 10^{+6.3(1/s-1)} \text{ for } s_i < 1 \quad (26b)$$

now with this model, the normal weighting scheme in equation (19) is modified:

$$\sigma_{shape}^2(a)=k^2[\sigma_c^2+(\sigma\lambda da/d\lambda)^2] \quad (27)$$

Higher errors are ascribed to the spectral regions exhibiting impurities. Hence data from the regions of the impurity are made less important in the derivation of the parameter vector p, equation (20).

The way that the scale factor, k, is defined, it doesn't matter whether the impurity is in the sample or the reference spectrum: any differences in shape between the two spectra automatically down-weight the region of the differences in the regression equation (20), placing more emphasis on the spectral regions with the common shape.

The following examples are intended to illustrate, but not limit, the invention disclosed herein.

EXAMPLE 1

Figure 3B:
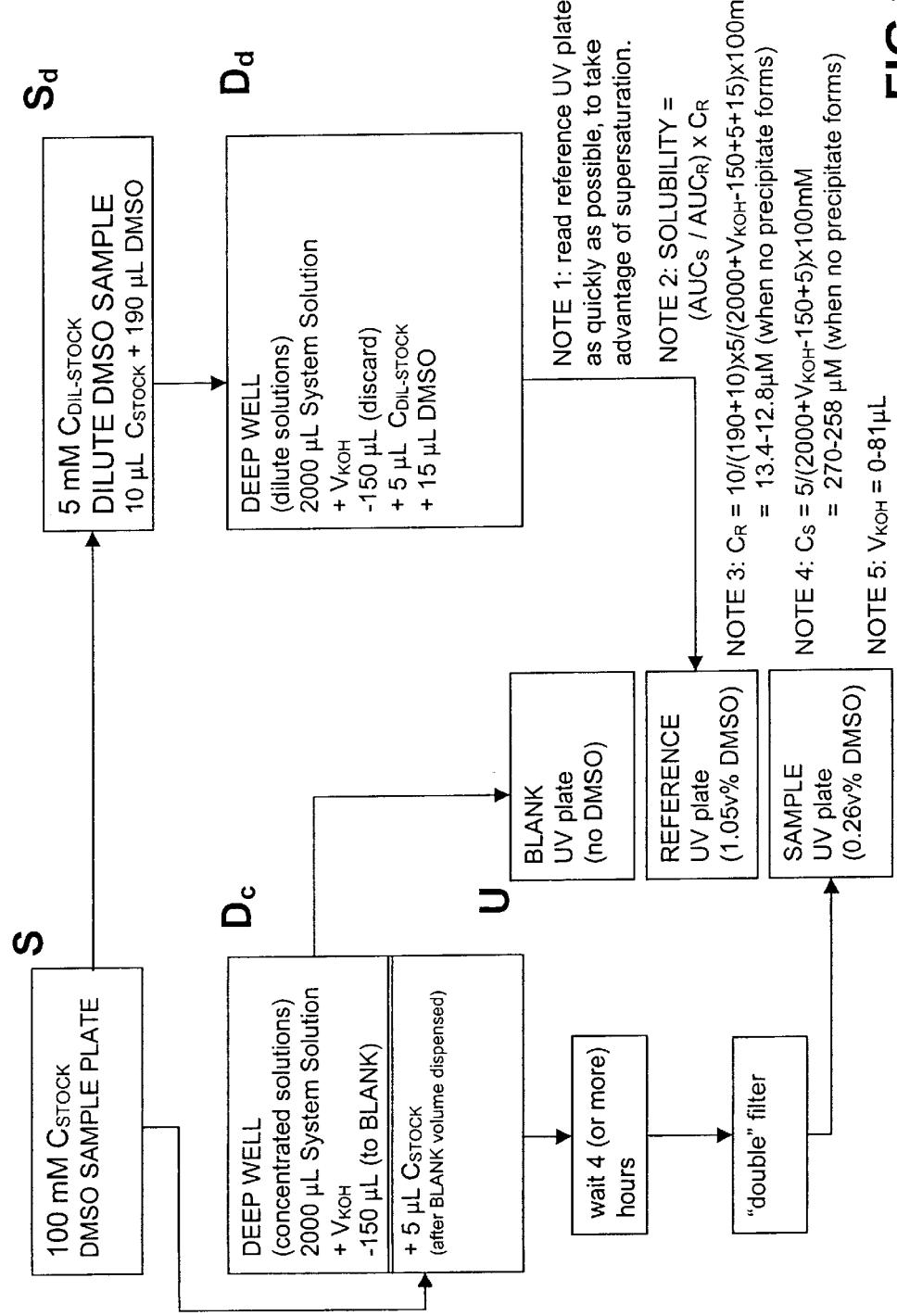

Apparatus of FIGS. 2 and 3: Solubility Determined by the Aqueous Dilution Method FIG. 2 summarizes the apparatus detailed below. The general aqueous dilution method used to determine solubility is described in FIG. 3a, and a specific embodiment is highlighted in FIG. 3b and detailed below.

Data Collection

1. The analytical device places 2.5 mL of universal buffer solution (25), initially at pH 3, into the side arm tube of a tall test tube 22 ("J-tube") located in the pH titrator assembly (3). An alkalimetric pH titration is performed.

2. Analysis of the titration data produces the pH values corresponding the titrant volumes 8, 16, 23, 30, 37, 44, 52, 59, 65, 73, 81 µL; these correspond closely to pH settings 3.0–8.5, in increments of 0.5 pH units. These volumes will be used by the device below.

3. The 96-well stock plate is placed in position 13 (S in FIG. 3b), furthest from operator on left rack on the robot table. Only one column of 8 sample wells will be used in this particular assay; for example, wells A1, B1, ..., H1 (or A2, B2, ..., H2, etc.) will contain the required compounds, 100 mM in DMSO in this example. This is the sample stock plate.

4. A new microtitre plate (must be inert to DMSO—NUNC 0.5 mL polypropylene is satisfactory) is placed in position 14 (Sd in FIG. 3b) rear position of the rack on the right. This is the empty reference stock plate.

5. A new 96-well deep plate (2.2 mL wells) is placed at position 15 (Dc in FIG. 3b), middle of the rack on the left on robot table.

6. A new 96-well deep plate (2.2 mL wells) is placed at position 16 (Dd in FIG. 3b), middle of the rack on the right on robot table.

7. A new 96-well Costar UV plate (or Greiner, but Costar is slightly better) is placed in position 17 (U), nearest to operator on left the rack on robot table.

8. A new rack of 20-µL disposable (conductive) pipet tips is placed into position 10 and a new rack of 200-µL disposable (conductive) pipet tips is placed in position 11 on the robot table.

9. A plastic waste bag is attached to the bottom of the waste-tip slide (12).

10. The system solution bottle needs to have at least 500 mL of the universal buffer solution.

11. A clean test tube in position 20, third test tube position nearest the operator of the test tube rack, is filled with 21 mL of DMSO. A clean test tube in position 21, second test tube position nearest the operator, is filled with 10 mL freshly prepared, low-carbonate, 0.5 M KOH.

12. Four clean test tubes, each containing 10 mL distilled water, are placed into positions 18.

13. The robot loads 1000 µL universal buffer solution into each of the deep 96-well plate in position 13 (Dc in FIG. 3b) on the table. Then the robot draws 0.5 M KOH from test tube in position 21 of the test tube rack. The robot proceeds to deposit 8 µL into the 8 deep wells A2-H2, 16 µL into deep wells A3-H3, 23 µL into deep wells A4-H4, 30 µL into deep wells A5-H5, 37 µL into deep wells A6-H6, 44 µL into deep wells A7-H7, 52 µL into deep wells A8-H8, 59 µL into deep wells A9-H9, 65 µL into deep wells A10-H10, 73 µL into deep wells A11-H11, and 81 µL into deep wells A12-H12.

14. Robot loads an additional 1000 µL universal buffer solution (25) into each of the deep wells, followed by extensive mixing.

15. Before any sample is added to 15 (Dc), the robot transfers 150 µL buffer solutions from the deep well to the UV plate in position 17 (U) on the table (Dc →U). The operator is prompted to take UV spectra of the buffer-filled UV plate, using the spectrophotometer (2). Afterwards, the UV plate is rinsed with methanol-water using the plate washer (5) and returned to position 17 (U), covered with a lid to keep dust out. This corresponds to the "blank" reading in equations (14) and (15).

16. To each of the deep wells (containing 1850–1931 µL pH buffer), 5 µL sample (27) is added, using the 20 µL tips 13→15 (S→Dc). The first sample pickup is discarded back into the stock plate, to ensure that the tip does not have an air gap at the opening and to ensure the dispenser stepper motor gears are free of slack, and that the inside surface of the tip is wetted before subsequent sample pickup. Vigorous "regurgitative" mixing follows. A protective cover is placed over 13 (S) plate after the transfers are complete.

17. The top of the deep well plate 15 (Dc) is sealed (aluminum plate seals), and the plate is placed on the orbital shaker (6) for 4 hours.

18. The robot transfers 190 µL DMSO to the empty reference stock plate 20→14. The robot transfers 10 µL samples: 13→14 (S→Sd). Solutions in Sd are thoroughly mixed. The sample stock plate 13 (S) may now be removed, protectively sealed, and stored in the refrigerator.

19. The robot loads 1000 µL universal buffer solution (25) into each well of the deep 96-well plate in position 16 (Dd) on the table. Then the robot draws 0.5 M KOH from test tube in position 21 of the test tube rack and proceeds to deposit 8 µL into the 8 deep wells A2-H2, 16 µL into deep wells A3-H3, 23 µL into deep wells A4-H4, 30 µL into deep wells A5-H5, 37 µinto deep wells A6-H6, 44 µL into deep wells A7-H7,52 µL into deep wells A8-H8, 59 µL into deep wells A9-H9, 65 µL into deep wells A10-H10, 73 µL into deep wells A11-H11, and 81 µL into deep wells A12-H12.

20. The robot loads an additional 1000 µL universal buffer solution (25) into each of the deep wells, followed by extensive mixing.

21. The robot discards 150 µL of each of the deep well solutions to waste. A second blank is not needed, but volumes in the deep well plate 16 (Dd) need to be the same those of 15 (Dc) after step 13.

22. To each of the deep wells, 15 µL DMSO are added 20→16.

23. To each of the deep wells (containing 1850–1931 µL pH buffer), 5 µL 20-fold diluted sample are added 14→16 (Sd→Dd). Vigorous mixing follows, a critical step.

24. As soon as mixing is complete in step 23, the robot transfers 150 µL of the reference solution to the UV plate 16→17 (Dd→U). Filtration is not necessary. The operator is prompted to take UV spectra of the UV plate, using 2. The deep well plate in position 16 (Dd) is no longer used. The UV plate is thoroughly washed on the plate washer 5 (using 75% methanol—25% water) and placed in position 17 (U), with a protective dust cover.

25. After the 4 hour shaking period elapses, the operator transfers the deep well plate from the orbital shaker to position 15 (Dc).

26. The operator places a used 96-well deep plate (2.2 mL wells) in the bottom of the vacuum manifold, position 4 on the robot table. On top of that the operator places a new 96-well deep filter plate (2.2 mL wells). The operator assembles the vacuum manifold accordingly. The robot transfers 20 $\mu$L precipitated solutions for the filtration step: 15→4. The operators is prompted to turn on the vacuum, to filter the solutions. This step pre-conditions the filters with sample, and is part of the so-called "double filtration" step.

27. The operator replaces the bottom (used) deep-well plate with a clean empty 96-well deep plate (2.2 mL wells) in the bottom of the vacuum manifold 4. On top of that the operator returns the sample-preconditioned 96-well deep filter plate (2.2 mL wells). The operator assembles the vacuum manifold again.

28. The robot transfers 250 $\mu$L saturated sample solutions for the filtration step: 15→4. Afterwards, the deep well filter plate in position 15 (Dc) may be sealed and stored for future examination or re-use.

29. The operators is prompted to turn on the vacuum, to filter the solutions, some of which may have solids in them. The operator discards the top deep-well filter plate and exposes the bottom deep-well plate for robotic access.

30. The operator removes cover on the UV plate at position 17 (U). The robot transfers 150 $\mu$L to the UV plate 4→17. The operator is prompted to take UV spectra of the UV plate. The deep well plate in position 4 may be discarded afterwards. If the plate 15 (Dc) is to be re-sampled later, then the UV plate should be thoroughly washed on the plate washer 5 (using 75% methanol—25% water) and placed in position 17 (U), with a protective cover, for future use. Blank and reference spectra need not be repeated in such re-samplings.

Data Processing

Figure 9:
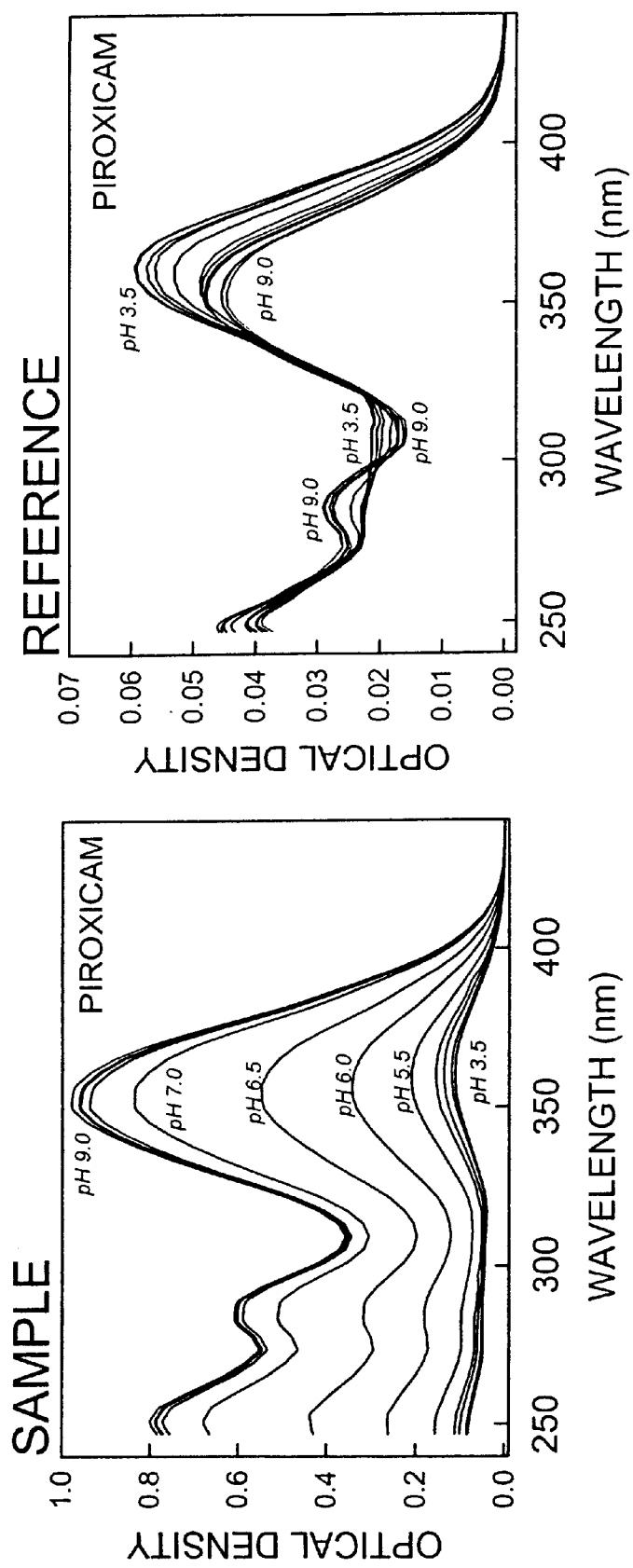
FIG. 9 shows UV spectra of piroxicam taken at several values of pH, typical of spectra taken in the aqueous dilution method. Note that the reference (right) absorbances are 20 times lower in optical densities, compared to the highest absorbances of the sample spectra (left).

FIG. 9 shows the measured absorption spectra due to piroxicam. The shown absorption spectra had been corrected for the absorption of "blank" plate, and for the absorption due to DMSO (equation 14).

For ionizable compounds, spectra can change dramatically as a function of pH. Also, at a given pH, if a portion of the sample precipitates, the optical density (OD) will decrease, following Beer's law.

FIG. 9 shows how spectra change with pH in the sample and reference solutions of piroxicam, a molecule which is effectively an ionizable acid if only the pH >3 is considered, with a p$K_a$ of 5.07 (Table 2). Both the sample spectra and the reference spectra are of excellent quality; however, one notes that the optical densities of the reference absorbance curves are relatively low (about OD 0.06 at the maximum), compared to those of the sample. If we had started out with 10 mM DMSO stock solutions, instead of 100 mM, the ODs would not have exceeded 0.006, a useable value, but one nearing the limit of detection. To produce a reference solution free of precipitate, it is necessary to compromise on sensitivity. Example 1 conditions have been demonstrated to work well. However, if 10 mM DMSO stock solutions are used, different DMSO stock plate dilutions need to be considered (S→Sd), along with different sampling volumes (S→Dc, Sd→Dd).

Example 2 below will show how the sensitivity issue can be avoided by using cosolvents.

As precipitation takes place to varying degrees in different pH values, the spectra of the sample solutions change in optical densities. This can be clearly seen in FIG. 9, where the sample spectra have the lowest OD values at pH 3.5 and systematically show higher OD values as pH is raised. The changing OD values indicate that solubility changes with pH.

The reference solutions only changes as a result of the ionization of the compound, and not due to changes in concentration of the compound. Usually ionization does not produce large changes in the OD values as a function of pH.

In the above example, the calculated reference solution concentrations in plate 16 (Dd in FIG. 3b or 35 in FIG. 3a) are $$C_R = 10/(190+10) \times 5/(2000 + V_{KOH} - 150 + 5 + 15) \times 100 \text{ mM} \quad (28)$$

$$= 12.8 - 13.4 \ \mu M$$

where $V_{KOH}$, the volume of 0.5 M KOH added to adjust the pH, varies from 0 to 81 $\mu$L.

Figure 5:
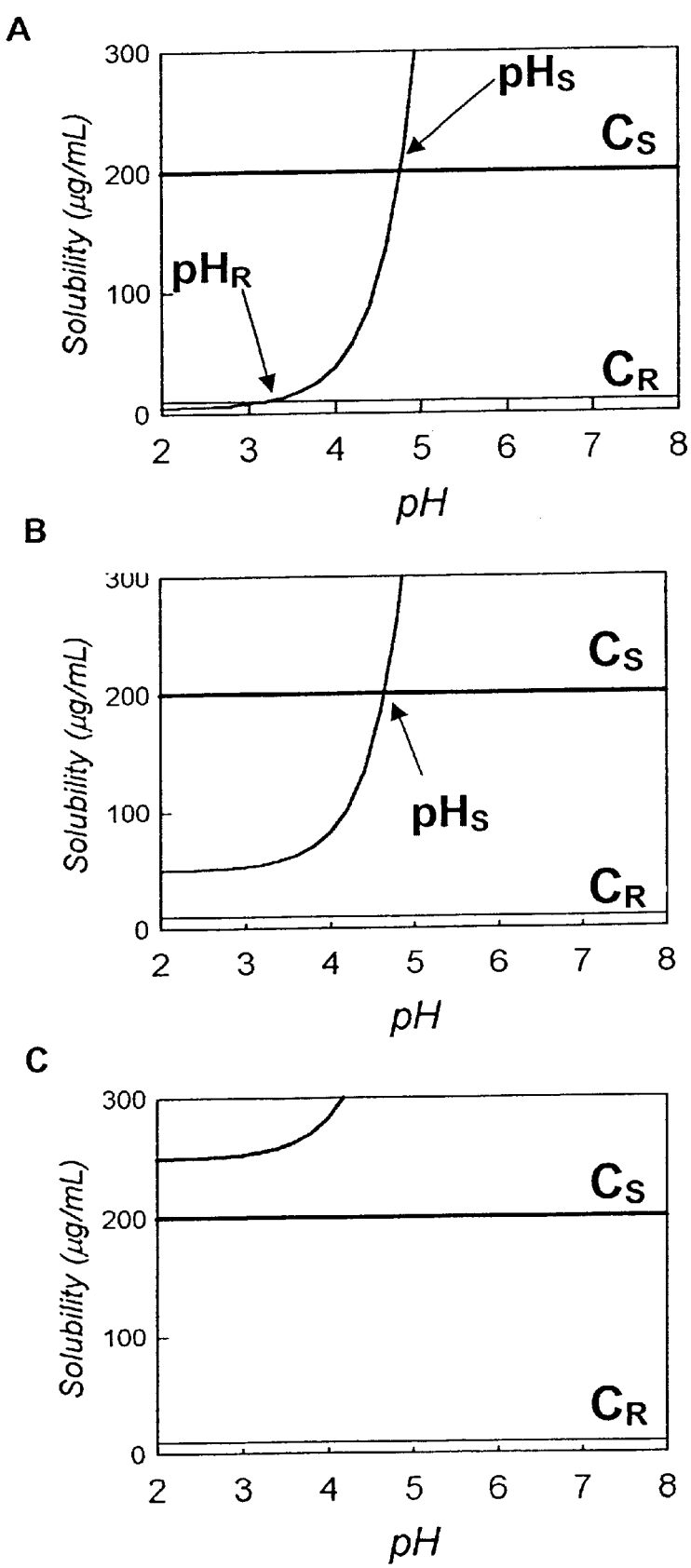
FIG. 5 illustrates the solubility—pH curve for a hypothetical ionizable acid with a $pK_a$ of 4 and three different intrinsic solubility values: (a) 5 µg/mL, (b) 50 µg/mL, and (c) 250 µg/mL. In each of the cases, the upper horizontal line represents the maximum possible sample solution concentration, and the lower horizontal line represents the maximum possible reference solution concentration, cf.

The reference concentrations are indicated by the lower horizontal lines in FIG. 5.

The limiting sample concentrations (assuming no precipitation had taken place in the deep-well plate 15 (31 in FIG. 3a or Dc in FIG. 3b) are calculated according to the formula $$C_s = 5/(2000 + V_{KOH} - 150 + 5) \times 100 \text{ mM} \quad (29)$$

$$= 258 - 270 \ \mu M \text{ (assuming no precipitate forms)}$$

The limiting concentration is represented by the horizontal lines in FIG. 7 and the upper horizontal lines in FIG. 5.

The next step requires that the spectra taken from 190 to 500 nm (in increments of 2 nm) be analyzed, to determine the area-under-the-curve (AUC) values, using equation (20) incorporating the shape-based weighting scheme, equation (27), in the analysis. With plastic UV plates, usually only the data in the interval 240–500 nm are actually used in the analysis. The optimized regression parameter is related R, the ratio of AUC values, equation (5).

Figure 6:
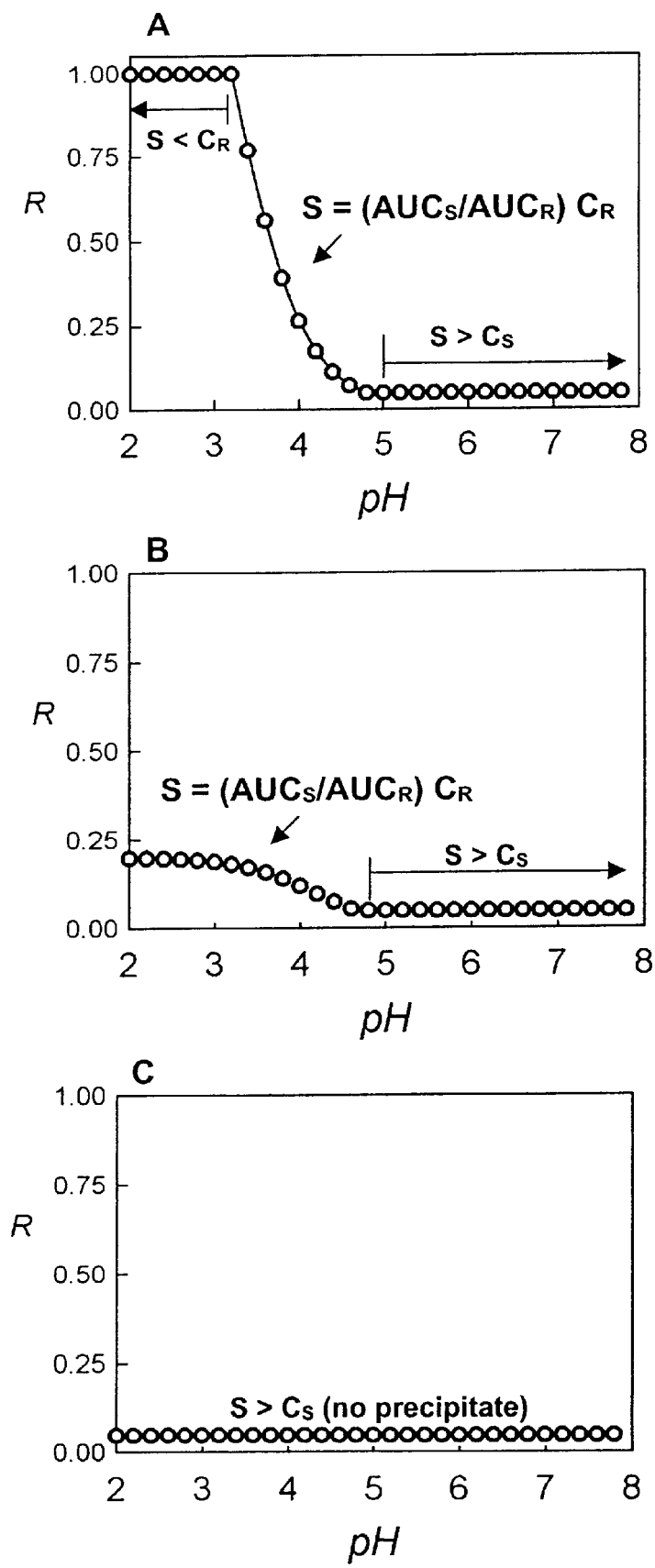
FIG. 6 below. Intersections of the lines with the curve form the working range of the aqueous dilution method for ionizable compounds.

If R=1 and the reference solution is not supersaturated, then one cannot report the solubility of the compound at the particular pH, since both the sample and the reference solutions have precipitation in them. This is indicated hypothetically in FIG. 5A for pH<p$H_R$, and in FIG. 6A by the low-pH region flat portion of the curve.

This situation is seldom seen in practice, since the quick handling of the reference plate and the higher amount of DMSO used in the reference plate compared to the sample plate almost always ensures that the sparingly soluble compounds are supersaturated. This is made more probable by the use of 1.06% v/v DMSO in the reference plate, compared to the usual 0.26% v/v DMSO in the sample deep well plate (in the latest variant of the protocol). On the other hand, the sample plate is allowed to sit for at least 4 hours, ample time in most cases for precipitation to start. The longer the wait time, the more "crystalline" the precipitated solid becomes.

An earlier version of the protocol used 0.5% v/v DMSO in both the reference and the sample deep well plates. The latest protocol (1.06% v/v DMSO in reference and 0.26% in sample) enhances the chances of supersaturation conditions in the reference deep well plates.

If R=10/(190+10)=0.05, then one cannot report the solubility of the compound at the particular pH, since both the sample and the reference solutions have no precipitate. This condition is common, and is indicated for all pH in FIG. 7A, for pH<8 in FIG. 7B, for pH<7 in FIG. 7C, for pH>6 in FIG. 7D, and for pH>6 in FIG. 7D. This corresponds to the hypothetical conditions for pH>pH$_S$ in FIG. 5A and FIG. 5B, and flat regions at the lowest parts of the curves in FIG. 6. To remedy this, one needs to use more concentrated DMSO stock solutions. This is not a problem in practice, since many discovery applications are mainly concerned with $C_S$<50 μg/mL. We demonstrated the aqueous dilution method with $C_S$ of 100 and 200 μg/mL (FIG. 7).

The R vs. pH relationships (FIG. 6) can be automatically assessed by the analytical device, and when the R is less than 1 but greater than 0.05, solubility is calculated according to equation (6). The useful pH domain for solubility determination are indicated in FIG. 5 as pH$_R$<pH<pH$_S$. In FIG. 7B, solubilities of amitriptyline can be determined for pH>8; in FIG. 7C, solubilities can be determined for pH>7, etc.

The minimum possible solubility refers to the intrinsic solubility, and such $S_o$ values often need to be extrapolated from the S vs. pH curve, taking its theoretical expected shape into account. The apparent intrinsic solubilities, $S_o^{APP}$ determined in this way are listed in Table 2, column 3, for the compounds used in the example. All the $S_o^{APP}$ values reported in Table 2 were determined in the presence of 0.5% v/v DMSO, except for phenazopyridine, where 0.26% was used.

Results of Aqueous Dilution Application

The most insoluble compounds were found to be terfenadine, miconazole, indomethacin, chlorpromazine, and piroxicam. We saw no evidence of precipitation with amiloride and nortriptyline, which suggests their solubilities are greater than 208 μg/mL and 98 μg/mL, respectively, in 0.5% v/v DMSO. Although we did see a few crystals in the propranolol well at pH 9.5, we were not able to derive the solubility with any confidence. We estimate that the solubility of propranolol is about 100 μg/mL in the presence of 0.5% v/v DMSO.

EXAMPLE 2

Apparatus of FIGS. 2, 4a, and 4b: Solubility Determined by the Cosolvent Method

FIG. 2 summarizes the apparatus detailed below. The general cosolvent method used to determine solubility is described in FIG. 4a, and a specific embodiment is highlighted in FIG. 4b and detailed below. In the variation utilizing cosolvent, all spectra were collected of solutions containing 50% v/v 1-propanol, but in other respects the methods are very similar.

Data Collection

1. The analytical device places 2.5 mL of universal buffer solution (25), initially at pH 3, into the side arm tube of a tall test tube 22 ("J-tube") located in the pH titrator assembly (3). An alkalimetric pH titration is performed.

2. Analysis of the titration data produces the pH values corresponding the titrant volumes 8, 16, 23, 30, 37, 44, 52, 59, 65, 73, 81 μL; these will correspond closely to pH settings 3.0–8.5, in increments of 0.5 pH units. These volumes will be used by the device below.

3. The 96-well stock plate is placed in position 13 (S in FIG. 4b), furthest from operator on left rack on the robot table. Only one column of 8 sample wells will be used in this particular assay; for example, wells A1, B1, . . . , H1 (or A2, B2, . . . , H2, etc.) will contain the required compounds, 100 mM in DMSO in this example. This is the sample stock plate.

4. A new microtitre plate (must be inert to DMSO—NUNC 0.5 mL polypropylene is satisfactory) is placed in position 14 (Sd in FIG. 4b) rear position of the rack on the right. This is the empty reference stock plate.

5. A new 96-well deep plate (2.2 mL wells) is placed at position 15 (Dc in FIG. 4b), middle of the rack on the left on robot table.

6. Test tube in position 19 (42 in FIG. 4a) is filled with 20–21 mL spectroscopic-grade 1-propanol.

7. A new 96-well Greiner UV plate (Greiner is better than Costar in the cosolvent method) is placed in position 17 (U), nearest to operator on left the rack on robot table.

8. A new rack of 20 μL disposable (conductive) pipet tips is placed into position 10 and a new rack of 200 μL disposable (conductive) pipet tips is placed in position 11 on the robot table.

9. A plastic waste bag is attached to the bottom of the waste-tip slide (12).

10. The system solution bottle needs to have at least 500 mL of the universal buffer solution.

11. A clean test tube in position 20, third test tube position nearest the operator of the test tube rack, is filled with 21 mL of DMSO. A clean test tube in position 21, second test tube position nearest the operator, is filled with 10 mL freshly prepared, low-carbonate, 0.5 M KOH.

12. Four clean test tubes, each containing 10 mL distilled water, are placed into positions 18.

13. The robot loads 1000 μL universal buffer solution into each of the deep 96-well plate in position 13 (Dc) on the table. Then the robot draws 0.5 M KOH from test tube in position 21 of the test tube rack. The robot proceeds to deposit 8 μL into the 8 deep wells A2-H2, 16 μL into deep wells A3-H3, 23 μL into deep wells A4-H4, 30 μL into deep wells A5-H5, 37 μL into deep wells A6-H6, 44 μL into deep wells A7-H7, 52 μL into deep wells A8-H8, 59 μL into deep wells A9-H9, 65 μL into deep wells A10-H10, 73 μL into deep wells A11-H11, and 81 μL into deep wells A12-H12.

14. Robot loads an additional 1000 μL universal buffer solution (25) into each of the deep wells, followed by extensive mixing.

15. Before any sample is added to 15 (Dc), the robot transfers 73 μL buffer solutions from the deep well to the UV plate in position 17 (U) on the table (Dc→U); the robot transfers 72 μL of 1-propanol from 19. The robot mixes the solvents in each well.

16. The operator is prompted to take UV spectra of the cosolvent-buffer-filled UV plate, using the spectrophotometer (2). The solution is SAVED and the plate is returned to position 17 (U), with its top tightly covered, to keep the dust out and evaporation minimized.

17. The robot transfers 190 μL DMSO to the empty reference stock plate 20→14. (1-propanol is not suitable at this point because of its volatility.) The robot transfers 10 μL samples using the 20 μL tips: 13→14 (S→Sd). Solutions in 14 (Sd) are thoroughly mixed.

18. As soon as the solutions are mixed in step 17, the robot transfers 5 μL from the diluted sample stock solution (using the 20 μL tips) to the blank solutions whose spectra had just been read in step 16: 14→17 (Sd→U). There are now 150 μL in each well of the Greiner plastic UV plate. The diluted sample stock plate 14 (Sd) may now be removed, protectively sealed, and stored in the refrigerator.

19. The operator reads the UV of the plate with the spectrophotometer 2. This becomes the reference plate reading. Discard the solutions and wash plastic UV plate thoroughly on the plate washer 5 (75% methanol—25% water). Place empty clean UV plastic plate in position 17 (U). Temporarily cover with lid to keep dust out.

20. To each of the deep wells at 15 (Dc) (containing 1927–2008 μL pH-adjusted universal buffer), 5 μL sample is added, using the 20 μL tips 13→15 (S→Dc). The first sample pickup is discarded back into the stock plate, to ensure that the tip does not have an air gap at the opening and to ensure the dispenser stepper motor gears are free of slack, and that the inner walls of the tip are wetted with sample. Vigorous "regurgitative" mixing follows. The sample stock plate 13 (S) may now be removed, protectively sealed, and stored in the refrigerator.

21. Seal the top of the deep well plate (aluminum plate seals), and place on the orbital shaker (6) for 4 hours.

22. The operator places a used 96-well deep plate (2.2 mL wells) in the bottom of the vacuum manifold (4). On top of that the operator places a clean 96-well deep filter plate (2.2 mL wells). The operator assembles the vacuum manifold accordingly. The robot transfers 20 μL precipitated solutions for the filtration step: 15→4. The operators is prompted to turn on the vacuum, to filter the solutions. This step, a part of the "double filtration" operation, pre-conditions the filters with sample.

23. The operator replaces the bottom (used) deep-well plate with a new 96-well deep plate (2.2 mL wells) in the bottom of the vacuum manifold. On top of that the operator returns the sample-preconditioned 96-well deep filter plate (2.2 mL wells). Operator assembles the vacuum manifold again.

24. The robot transfers 250 μL precipitated sample solutions for the filtration step: 15→4. Afterwards, the deep well filter plate in position 15 (Dc) may be stored for future examination or re-use.

25. The operators is prompted to turn on the vacuum, to filter the solutions, some of which may have solids in them. The operator discards the top deep-well filter plate and exposes the bottom deep-well plate for robotic access.

26. The operator removes cover on the UV plate at position 17 (U). The robot transfers 75 μL of the filtered sample solution to the UV plate: 4→17. Immediately following that, the robot transfers 75 μL 1-propanol to the UV plate: 19→17. The solutions are thoroughly mixed.

27. The operator is prompted to take UV spectra of the UV plate (17→2). The UV plate and the deep well plate in position 4 are discarded afterwards.

Data Processing

Figure 10A:
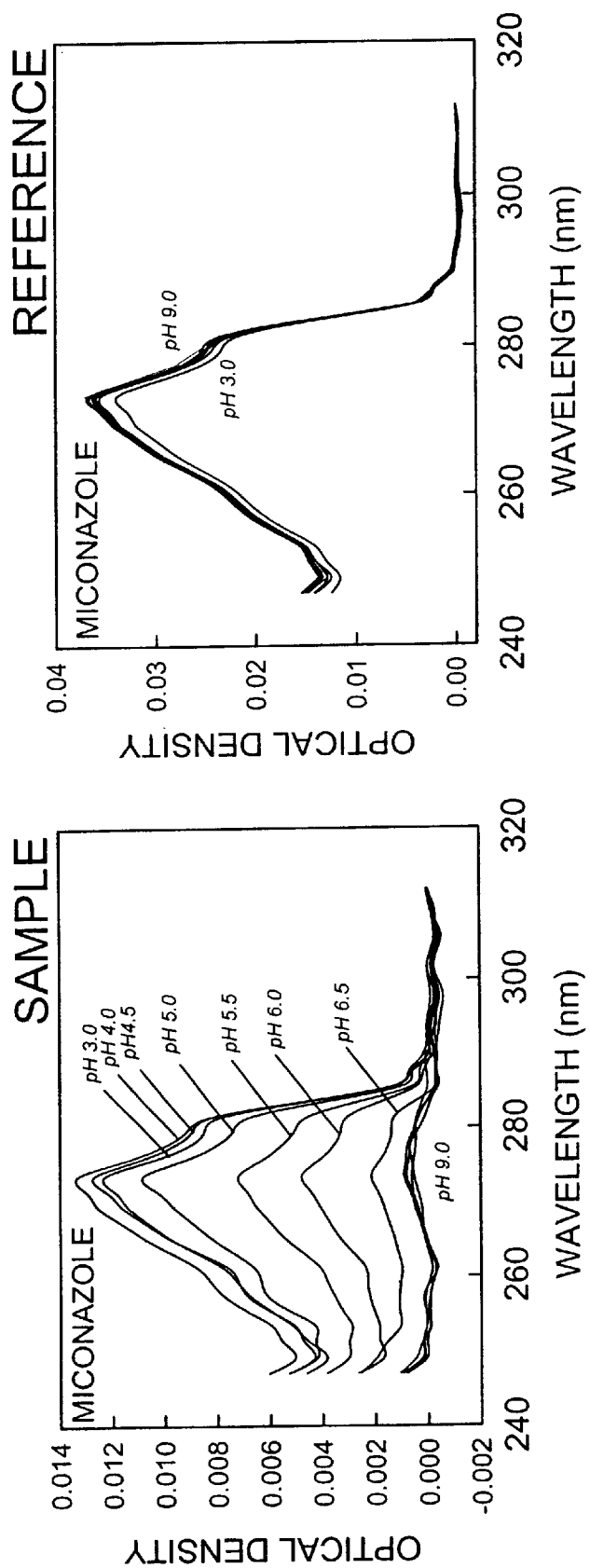
FIG. 10 shows UV spectra of (a) miconazole and (b) phenazopyridine, taken at several values of pH, typical of spectra taken in the cosolvent method. Note that the reference (right) absorbances are slightly higher than the highest sample absorbances (left), in contrast to the situation in the aqueous dilution method (FIG. 9). In principle, this indicates that the cosolvent method is more sensitive than the aqueous dilution method.
Figure 10B:
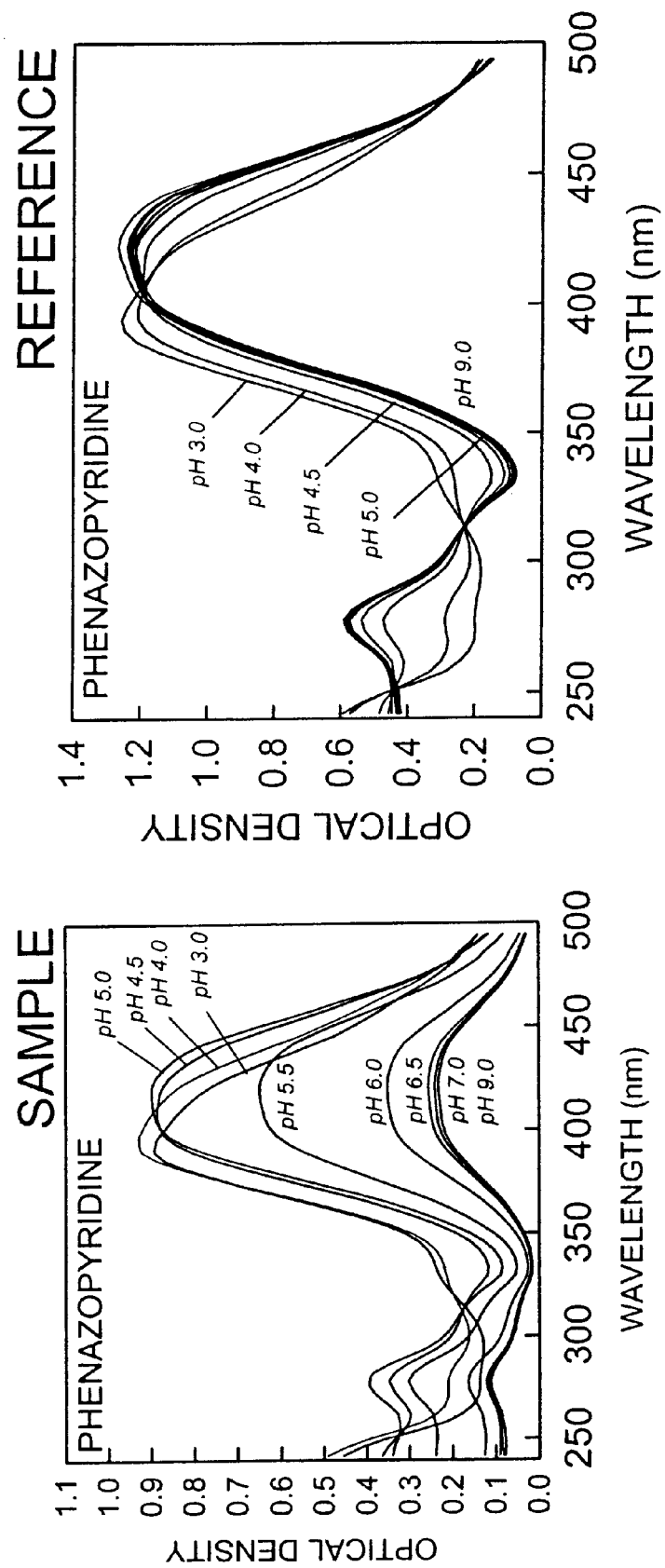

FIG. 10a shows the measured absorption spectra of miconazole, and FIG. 10b shows those of phenazopyridine. The shown absorption spectra had been corrected for the absorption of the "blank" plate, and for the absorption due to DMSO (equation 14).

For ionizable compounds, spectra can change dramatically in shape as a function of pH, as in the reference spectra in FIG. 10b, but this isn't always so, as illustrated by the spectra of miconazole in FIG. 10a.

The reference solutions only changes as a result of the ionization of the compound, and not due to changes in concentration of the compound.

Also, at a given pH, if a portion of the sample precipitates, the optical density (OD) will decrease, following Beer's law, which is what all the sample spectra in FIGS. 9 and 10 show.

FIG. 10a shows how spectra change with pH in the sample solutions of miconazole, an ionizable base with a $pK_a$ 6.07 (Table 2). Both the sample spectra and the reference spectra are of excellent quality, with the optical densities of the reference absorbance curves being comparable to those of the sample. This is one of the advantages of the cosolvent method over the aqueous dilution method, in that sensitivity is similar in the sample and reference solutions.

One of the disadvantages of the cosolvent method is that of the increased evaporation of the cosolvent-containing solution. Nevertheless, example 2 conditions have been demonstrated to work well. However, if 10 mM DMSO stock solutions are used, different DMSO stock plate dilutions need to be considered (S→Sd).

As precipitation takes place to varying degrees in different pH values, the spectra of the sample solutions change in optical densities. This can be clearly seen in FIG. 10a for the sample spectra, where the sample spectra have the lowest OD values at pH 9.0 and systematically show higher OD values as pH is lowered, a pattern consistent with that of an ionizable base. The changing OD values indicate that solubility changes with pH. FIG. 10b is that of an ionizable acid, and so the pH—OD trend in the sample spectra follow the reverse order.

In the above example, the calculated reference solution concentrations, after the cosolvent had been added in step 18 (48 in FIG. 4a) above, are $$C_R^{COS} = 10/(190+10) \times 5/(145+5) \times 100 \text{ mM} \quad (30)$$
$$= 167 \text{ } \mu M$$

Note that this is nearly ten times higher than the value in the aqueous dilution method (equation 28).

The limiting sample concentrations (assuming no precipitation had taken place in the deep-well plate 15 (Dc) and in solution 43 in FIG. 4a) are calculated according to the formula $$C_S^{COS} = 75/150 \times 5/(2000 + V_{KOH} - 73 + 5) \times 100 \text{ mM} \quad (31)$$
$$= 248 - 259 \text{ } \mu M \text{ (assuming no precipitate forms)}$$

The next step requires that the spectra taken from 190 to 500 nm (in increments of 2 nm) be analyzed, to determine the area-under-the-curve (AUC) values, using equation (20) incorporating the shape-based weighting scheme, equation (27), in the analysis. With plastic UV plates, usually only the data in the interval 240–500 nm are actually used in the analysis. The needed regression parameter is $R^{COS}$, the ratio of AUC values, equation (7).

The same considerations need to be made with regards to the limiting cases of the $R^{COS}$ ratios, as was discussed in the aqueous dilution method.

The R=1 situation (precipitate in both 43 and 48 in FIG. 4a) is very rarely seen in practice, since the quick handling of the reference plate and the higher amount of DMSO used in the reference plate compared to the sample plate almost always ensures that the sparingly soluble compounds are supersaturated if not dissolved. This is made more probable by the use of 3.33% v/v DMSO in the reference plate, compared to the 0.26% v/v DMSO in the sample deep well plate, and by the added cosolvent, 1-propanol at 50% v/v. In effect, there are fewer restrictions in the cosolvent method. Volatility of the cosolvent is the main disadvantage, as said before.

The solubility is calculated according to equation (8). The results for phenazopyridine stated in Table 2 were determined by the cosolvent method.

EXAMPLE 3

Aqueous Solubility Determined From the Shifts in $pK_a$ in the Presence of Non-ionizable Chemicals that Distort the Solubility-pH Profiles.

The apparent solubilities determined by equations (6) and (8) are plotted in FIG. 7 as the points below the horizontal lines. Those points are replotted in FIG. 8 as log $S^{APP}$ vs. pH. The solid curves in FIG. 8 are the results of fitting the apparent solubilities to standard equations described in the Background section. From that analysis, it was possible to obtain $pK_a^{APP}$ and $S_o^{APP}$ values. The latter apparent intrinsic solubility constants are listed in Table 2.

As a visual check, the apparent ionization constants may be estimated as the pH values at the intersections of the horizontal and diagonal asymptotes of the solid curves.

Since the $pK_a$s of the studied compounds are known (Table 2), it was possible to calculate the $pK_a$ shifts (Δ values in Table 1). These shifts were used to calculate the corrected aqueous intrinsic solubilities, $S_o$, also listed in Table 2.

As one can see in all plots in FIG. 8, DMSO/aggregation has a significant influence on the intrinsic solubility even in 0.5% v/v DMSO. Most of the $pK_a$s were shifted by up to one log unit. As far as we could find, this had not been recognized before in DMSO-containing solutions. Nor had a method been put forward that could correct for this effect (cf., Table 1). Table 2 summarizes the results of the corrective calculations, and compares the results to literature values. The comparison is especially good for terfenadine, probenecid, miconazole, and furosemide.

a. Chlorpromazine

The ionizable base chlorpromazine has a $pK_a$ of 9.24 (Table 2). From the solid curve in FIG. 8, the apparent $pK_a$ is 8.48, which is a $pK_a$ shift of −0.76, consistent in sign with the expected behavior of bases. According to equation (11), $$\log S_o = \log 19.4\ \mu g/mL - 0.76 = 0.528 \quad (32)$$

or $$S_o = 10^{+0.528} = 3.4\ \mu g/mL \quad (33)$$

The horizontal asymptote in the dashed curve corresponding to chlorpromazine in FIG. 8 is 0.528 (log scale), corresponding to 3.4 μg/mL. This value is in excellent agreement with the value determined with the pSOL instrument, and is in reasonable agreement with the shake-flask value (Table 2). We cannot say with certainty that the $pK_a$ shift is due solely to the effect of DMSO, or due solely to aggregation, since chlorpromazine is known to be surface-active. However, the method of our invention does not require the knowledge of the source of the effect. The method simply corrects solubilities according to the scheme in Table 1.

b. Piroxicam

The ionizable acid piroxicam (considering pH>3) has a $pK_a$ of 5.07 (Table 2). From the solid curve in FIG. 8, the apparent $pK_a$ is 6.05, which is a $pK_a$ shift of +0.98, consistent in sign with the expected behavior of acids. According to equation (10), $$\log S_o = \log 10.5\ \mu g/mL - 0.98 = 0.041 \quad (34)$$

or $$S_o = 10^{+0.041} = 1.1\ \mu g/mL \quad (35)$$

The horizontal asymptote in the dashed curve corresponding to piroxicam in FIG. 8 is 0.041 (log scale), corresponding to 1.1 μg/mL. This value is in poor agreement with the values determined by the shake-flask method (Table 2), 9.1 and 8–16 μg/mL. Both of the latter values were determined in the absence of DMSO. The inspection of the log S vs. pH data corresponding to the former value indicated a positive $pK_a$ shift. Application of the correction yielded the value 3.3 μg/mL, a considerable improvement. The 8–16 μg/mL reported value did not reveal detailed log S vs. pH data. However, the authors did indicate that the $pK_a$ was deduced from the data as 5.63. This would suggest the expected positive shift, and the corrected intrinsic solubility is thus 2.2–4.4 μg/mL, in very good agreement with the other 1.1 and 3.3 μg/mL values.

TABLE 2

Intrinsic Solubility, $S_o$, Corrected for the Drug-DMSO/Drug-Aggregate Effects

| compound | $pK_a$ | $S_o^{APP}$ (μg/mL) | corrected $S_o$ (μg/mL) | pSOL $S_o$ (μg/mL) | Shake-Flask $S_o$ (μg/mL) |
|---|---|---|---|---|---|
| amitriptyline | 9.45[a] | 56.9 | 3.0 | 2.0[a] | 2.0[a] |
| chlorpromazine | 9.24[a] | 19.4 | 3.4 | 3.5[a] | 0.1[a] |
| diclofenac | 3.99[b] | 22.6 | 3.8 | 0.8[b] | 0.6[b] |
| furosemide | 10.63, 3.52[b] | 29.8 | 2.9 | 5.9[b] | 12.0[b] (2.9[c]) |
| griseofulvin | non-ionizable | 37.6 | 20.2 | | 9[d] |
| indomethacin | 4.42[a] | 7.2 | 4.1 | 2.0[a] | 2.0[a], 1[e] |
| miconazole | 6.07[f] | 11.1 | 1.6 | 0.7[f] | |
| 2-naphthoic acid | 4.16[f] | 33.3 | 20.2 | | 22.4[g] |
| phenazo-pyridine | 5.15[f] | 12.2 | 12.2 | 14.3[f] | |
| piroxicam | 5.07, 2.33[h] | 10.5 | 1.1 | | 9.1[i] (3.3[c]), 8–16[j] (2.2–4.4[c]) |
| probenecid | 3.01[f] | 4.6 | 0.7 | 0.6[f] | |
| terfenadine | 9.53[f] | 4.4 | 0.1 | 0.1[f] | |

[a]M. A. Strafford, A. Avdeef, P. Artursson, C. A. S. Johansson, K. Luthman, C. R. Brownell, R. Lyon, Am. Assoc. Pharm. Sci. Ann. Mtng. 2000, poster presentation.
[b]A. Avdeef, C. M. Berger, C. Brownell, Pharm. Res. 2000, 17, 85–89.
[c]Corrected for aggregate formation: unpublished data.
[d]J. Huskonen, M. Salo, J. Taskinen, J. Chem. Int. Comp. Soc. 1998, 38, 450–456.
[e]S. H. Yalkowsky, R. -M. Dannenfelser (Eds.), AQUASOL dATAbASE of Aqueous Solubility, 5th Ed., 1998, College of Pharmacy, Univ. of Arizona, Tucson, AZ 85721.
[f]pION, unpublished data.
[g]K. G. Mooney, M. A. Mintun, K. J. Himmestein, V. J. Stella, J. Pharm. Sci. 1981, 70, 13–22.
[h]A. Avdeef, K. J. Box, Sirius Technical Application Notes, Vol. 2, 1996, p. 110.
[i]C. R. Brownell, FDA, private correspondence, 2000.
[j]J. Jinno, D. -M. Oh, J. R. Crison, G. L. Amidon, J. Pharm. Sci. 2000, 89, 268–274 (24 hr).

c. Phenazopyridine

Phenazopyridine is an interesting molecule. It is an ionizable base, but it has positive $pK_a$ shifts. The true $pK_a$ is 5.15, but in saturated solutions, containing 0.26% v/v DMSO, the apparent $pK_a$ is 5.83. We believe that this is a case where positively charged species either interact with DMSO or form aggregates. Being charged species, the effect is to shift the diagonal segment of the curve in a horizontal direction in the log S vs. pH plot, as indicated by the dashed line in FIG. 8. This means that the intrinsic solubility constant is not affected (Table 1).

We found a similar example in the literature for prostaglandin F2α (Table 1). The molecule is an acid, but shows a negative $pK_a$ shift. The authors proposed that micelles formed to cause the shift. No effort was made to characterize the apparent $pK_a$. As in the case of phenazopyridine, the intrinsic solubility is not affected by the aggregation of negatively-charged species.

EXAMPLE 4

Shape-based Weighting Scheme Applied to Solubility Determination

Figure 11:
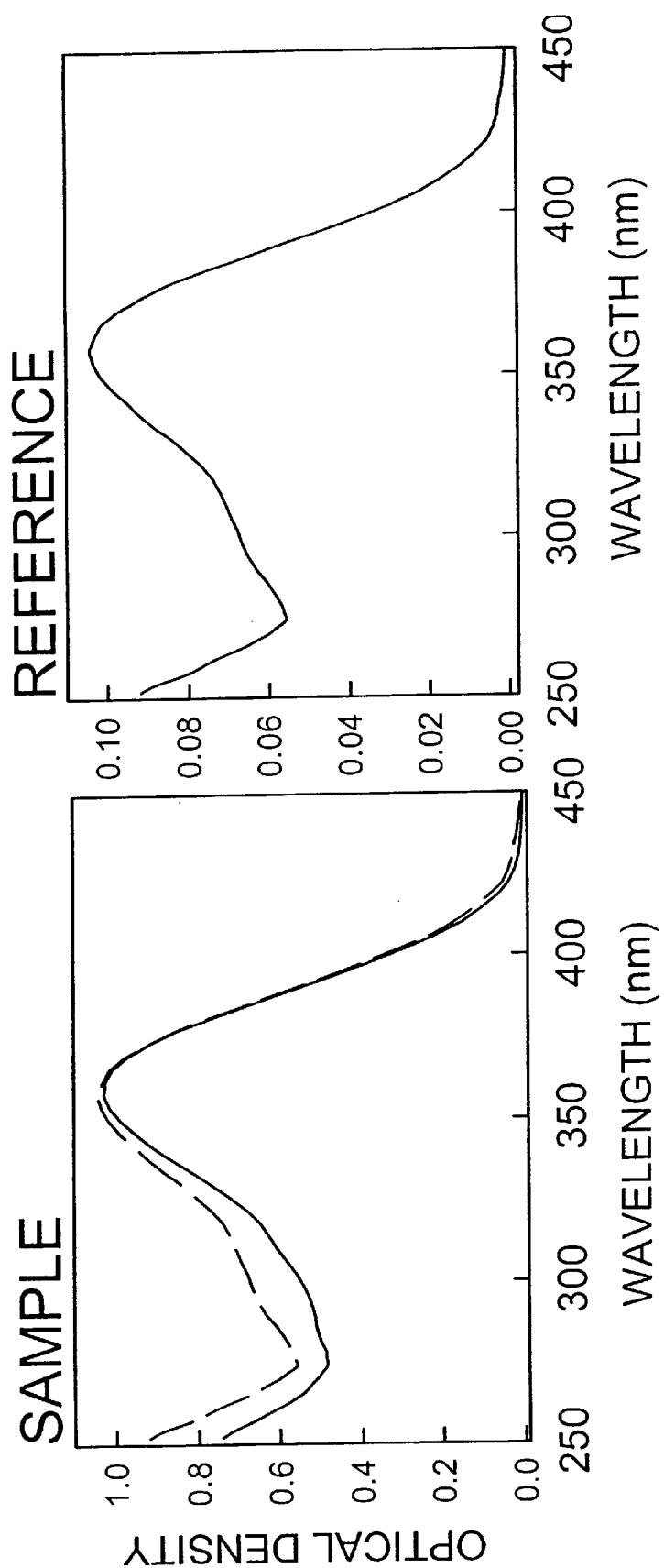
FIG. 11 shows sample and reference spectra, where there is a shape difference in the region of 250–350 nm. The special weighting scheme, equation 27 below, down-weights the data in the region of 285 nm by a factor of 169. Multiplying the reference curve by 10 and superimposing it on the sample curve produced the dashed curve.

Let's consider the example in FIG. 11. Shown are the spectra of a sample and a reference solution of piroxicam. The peak maximum occurs at 359 nm. Consider the point in the spectra at 285 nm, where there is a pronounced difference in shapes between the reference spectrum and the sample spectrum. The normal error at 285 nm is calculated by equation (23) to be 0.0007 absorbance unit. For this example, $$r_i^{REF} = a_i^{REF}/a_{max}^{REF} = 0.06/0.104 = 0.577 \quad (36)$$

$$r_i^{SAMPLE} = a_i^{SAMPLE}/a_{max}^{SAMPLE} = 0.50/1.025 = 0.488 \quad (37)$$

$$s_i = |r_i^{SAMPLE}/r_i^{REF}| = 0.488/0.577 = 0.944 \quad (38)$$

$$k_i = 10^{+6.3(1/s-1)} = 13 \quad (39)$$

So, the shape-biased error is a assigned to be 13 times higher in the region of shape discordance, namely, 0.008. Hence, the region near 285 nm is down-weighted by a factor of $13^2$, or 169. In effect, when peak shape differences are encountered, the data are automatically taken out of consideration in the determination of the p-vector in the weighted linear regression analysis.

EXAMPLE 5

Shape-based Weighting Scheme Applied to Permeability Determination

The shape-based weighting scheme we developed is general and can be applied to any spectroscopic determination of concentrations using multi-wavelength data. We have applied the UV-based shape analysis weighting scheme to the determination of permeability constants. This scheme is also applicable to any concentration determination using spectral data.

EXAMPLE 6

Improved Aqueous Universal Buffer Formulation Possessing Low-UV Components and Being Free of Phosphate and Citrate In this example and in Example 7 below, two new improved universal buffers are described for high-throughput solubility applications, and other applications where concentration measurements are made at controlled pH using spectrophotometric methods, including permeability measurements. We sought to discover an aqueous and a cosolvent-water universal buffer which would make solubility measurements more reliable. We wanted buffers that would not interact with the molecules being studied, which meant that the background salt concentrations needed to be low. For this reason, we had to stay away from phosphate as a buffer component due to its strong tendency to cause salts of positively-charged drug substances to precipitate [W. H. Streng, S. K. Hsi, P. E. Helms, H. G. H. Tan, *J. Pharm. Sci.* 1984, 73, 1679–1684]. We wanted to avoid ion-pair interactions between buffer components and the sample, so we wanted to stay away from lipophilic buffers. Since we wanted our detection system to obtain as much signal due to sample and as little due to background buffers, we wanted the UV absorption due to the buffer to be as low as possible. Citric acid buffer component would not have been a good choice from this consideration. We wanted the pH vs. volume of alkaline titrant relationship to be as linear as possible, so that we could easily predict how much of a pH change a given sample may impart on the buffer system.

None of the commonly known universal buffers [D. D. Perrin, B. Dempsey, *Buffers for pH and Metal Ion Control*, Chapman and Hall, London, 1974; A. Avdeef, J. J. Bucher, *Anal. Chem.* 1978, 50, 2137–2142] fit the desired profile. We found that the zwitterionic Good's buffers [Good, Winget, Winter, Connolly, Izawa, Singh, *Biochemistry* 1966, 5, 467] best fit our desired characteristics. Several buffers were tested as possible candidates, but one set was discovered to be outstanding.

The best candidates for the aqueous universal buffer were discovered to be the combination: acetic acid, MES(4-morpholine-ethanesulfonic acid), HEPES(4-(2-hydroxyethyl)-1-piperazineethanesulfonic acid), and boric acid. MES and boric acid had virtually no UV absorption above 210 nm. HEPES and acetic acid had $pK_a$s in the right positions to make them attractive choices, even though their UV absorptivities were not the lowest.

Each component was initially chosen to be 5 mM, to form an equimolar mixture, but better ratios were discovered afterwards.

TABLE 3

Composition of the Aqueous Universal Buffer[a]

| Buffer Component | MW | Weight (g) Used to Make 1 L | Concentration (mM) | $pK_a$ (I = 0.020M[b]) |
|---|---|---|---|---|
| Sodium Acetate, Trihydrate | 136.08 | 0.7626 | 5.60 | 4.64 |
| MES monohydrate | 213.26 | 1.0286 | 4.82 | 6.08 |
| HEPES | 238.31 | 1.1915 | 5.00 | 7.48, 3.01 |
| Boric Acid | 61.83 | 0.4083 | 6.60 | 9.13 |

[a]To achieve a starting pH 3.0, 16.26 mL of 0.5 M HCl were added per liter, corresponding to 0.008 M added HCl.
[b]I = average ionic strength in the titration from pH 3–10.

Figure 12:
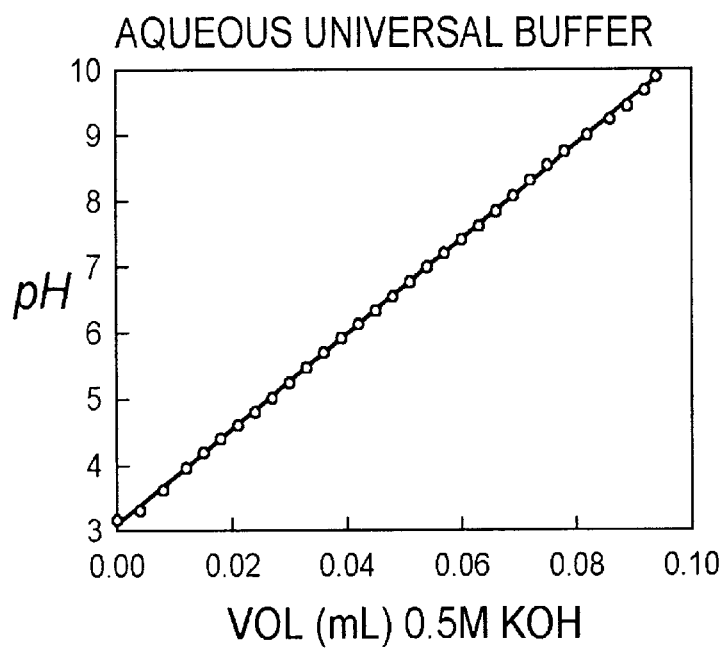
FIG. 12 shows the alkalimetric pH titration curve of the aqueous universal buffer solution.

Table 3 shows the best component concentrations, along with other properties of the components. Obviously, other forms of the buffering materials (e.g., sodium acetate, anhydrous) could be utilized. FIG. 12 shows the pH-volume curve, where 2.00 mL of aqueous universal buffer solution were titrated with 0.5 M KOH.

The linear regression of pH vs. titrant volume produced the equation: pH=3.10+72.08 $V_{KOH}$, with the extraordinary standard deviation of 0.02 pH units.

EXAMPLE 7

Improved Aqueous-Cosolvent Universal Buffer Formulation Possessing Low-UV Components and Being Free of Phosphate and Citrate Finding suitable candidates for a cosolvent universal buffer solution was problematic, since cosolvents change the $pK_a$s of the buffer components, and it is difficult to predict accurately to what extent the $pK_a$s would be different. The best candidates for the cosolvent buffer (Table 4), where the cosolvent acetonitrile was mixed with water in 1:1 proportion were discovered to be glycolic acid, MES, HEPES, and taurine (2-aminoethanesulfonic acid).

Figure 13:
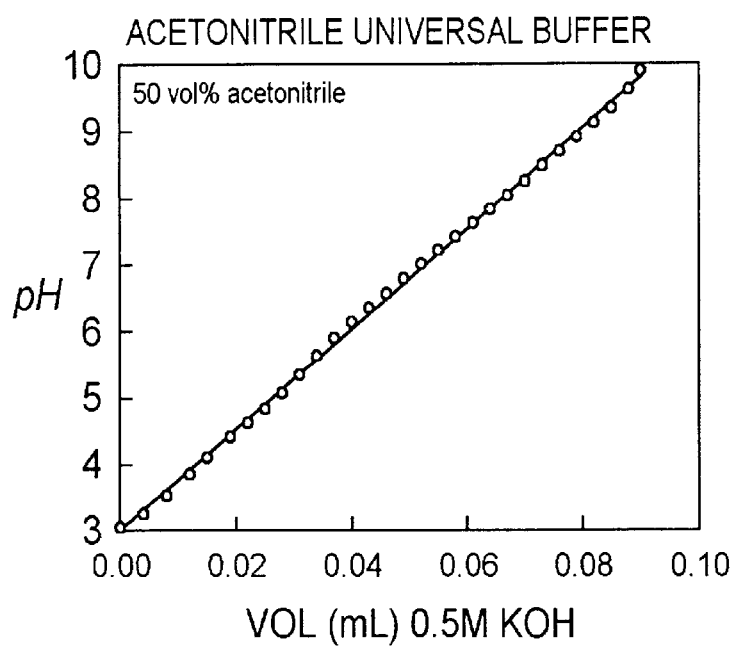
FIG. 13 shows the alkalimetric pH titration curve of the cosolvent-water universal buffer solution.

FIG. 13 shows the pH-volume curve, where 2.00 mL of acetonitrile-water universal buffer solution were titrated with 0.5 M KOH. The linear regression of pH vs. titrant volume produced the equation: pH=3.01+75.59 $V_{KOH}$, with a good standard deviation of 0.06 pH units.

TABLE 4

Composition of the 1:1 Acetonitrile-Water Universal Buffer[a]

| Buffer Component | MW | Weight (g) Used to Make 1 L | Concentration (mM) | $pK_a$ (I = 0.012 M, 50 vol % $CH_3CN$) |
|---|---|---|---|---|
| Glycolic Acid | 76.05 | 0.4000 | 5.26 | 4.56 |
| MES monohydrate | 213.26 | 1.0000 | 4.69 | 6.24 |
| HEPES | 238.31 | 1.1915 | 5.00 | 7.54, 2.91 |
| Taurine | 125.15 | 0.7000 | 5.60 | 8.95 |

[a]To achieve a starting pH 3.0, 6.76 mL of 0.5 M HCl were added per liter, corresponding to 0.003366 M added HCl. Initially, 500 mL acetonitrile was added to the weighed components in a 1 L volumetric flask, to which were added 6.76 mL 0.5M HCl. Distilled water was then added to make 1.00 L solution.

Variations of the above methods and analytical devices will be apparent to those with ordinary skill in the field.

We claim:

1. A method for high-throughput spectrophotometric measurement of the aqueous solubility of a compound, said compound having limited solubility in an aqueous buffer, not requiring knowledge or measurement of the molar absorptivity of said compound, and not requiring a calibration curve relating known concentrations of said compound to spectrophotometric properties of said compound, comprising:
   a. preparing a sample solution of said compound in an aqueous buffer of known pH, and separating said sample solution from any precipitate,
   b. preparing a reference solution that has a known concentration of said compound in said buffer, under conditions avoiding or suppressing precipitation,
   c. preparing a blank solution free of said compound, but otherwise of the same composition as said reference solution,
   d. measuring a spectrophotometric property of said sample, reference, and blank solutions, with or without further dilution thereof with cosolvent, wherein said cosolvent possesses one or more of the properties selected from the group consisting of (1) high capacity to dissolve said compound, (2) low UV absorption, and (3) low vapor pressure and
   e. determining the concentration of said sample solution by comparing the measured spectrophotometric property of said sample, reference and blank solutions, and calculating from said determination the aqueous solubility of said compound if said sample solution constitutes a saturated solution.

2. The method of claim 1, wherein said spectrophotometric property is selected from the group consisting of UV range spectrophotometry, visible range spectrophotometry, colorimetry, polarimetry, optical rotation, fluorimetry and circular dichroism detection.

3. The method of claim 1 wherein:
   a. said reference solution is prepared by dissolving a known quantity of said compound or stock solution containing said compound in a known volume of said buffer wherein a calculated concentration of said reference solution is known, and wherein said calculation ignores any precipitation of said compound, and
   b. said sample solution is prepared by dissolving a known quantity of said compound or stock solution containing said compound in a known volume of said buffer wherein a calculated concentration of said sample solution is known and is greater than said calculated concentration of said reference solution, and wherein said calculation ignores any precipitation of said compound, said method comprising
      (1) determining a ratio equal to said measured spectophotometric property of said reference solution divided by said measured spectrophotometric property of said sample solution, said properties corrected for said specrophotometric property of said blank solution,
      (2) determining a factor equal to said calculated concentration of said reference solution divided by said calculated concentration of said sample solution, wherein said solubility is equal to
         (a) said calculated concentration of said reference solution divided by said ratio when said ratio is either greater than 1, or is less than 1 but greater than said factor,
         (b) or is less than said calculated concentration of said reference solution when said ratio is equal to 1,
         (c) or is greater than said calculated concentration of said sample solution when said ratio is equal to said factor.

4. The method of claim 1 wherein said compound is presented as a stock solution in DMSO and said spectrophotometric property is UV range absorbance.

5. The method of claim 4 wherein:
   a. said reference solution is prepared by adding an aliquot of said stock solution to a volume of DMSO and then adding a portion of that DMSO solution to a volume of aqueous buffer, and
   b. said sample solution is prepared by adding an aliquot of said stock solution to a volume of said buffer, after which said sample solution is separated from any precipitate.

6. The method of claim 5, wherein:
   a. said reference solution is prepared by diluting 1 aliquot of said stock solution with 19 aliquots of DMSO; and 1 aliquot of said diluted solution is further diluted with 3 aliquots of DMSO and 400 aliquots of said buffer,
   b. said sample solution is prepared by diluting 1 aliquot of said stock solution with 400 aliquots of said buffer, allowing said solution to equilibrate for several hours, after which any insoluble compound is separated from said sample solution,
   c. said method comprising determining a ratio equal to said measured spectophotometric property of said reference solution divided by said measured spectrophotometric property of said sample solution, said properties corrected for said specrophotometric property of said blank solution, wherein said solubility is equal to
      (1) said calculated concentration of said reference solution divided by said ratio when said ratio is either greater than 1, or is less than 1 but greater than 1/20 factor,
      (2) or is less than said calculated concentration of said reference solution when said ratio is equal to 1,
      (3) or is greater than said calculated concentration of said sample solution when said ratio is equal to 1/20 factor.

7. The method of claim 4, wherein
a. said blank is prepared by diluting said buffer with said cosolvent,
b. said reference solution is prepared by diluting stock solution with DMSO, said butter, and said cosolvent to avoid or suppress any precipitation, wherein a calculated concentration of said reference solution is known,
c. said sample solution is prepared by diluting stock solution with said buffer, separating said sample solution from any precipitate, wherein a calculated concentration of said sample solution is known, wherein said calculation ignores any precipitation, and
d. further diluting said sample solution with said cosolvent, wherein the term 1+Y/Z, where Y is the volume of said cosolvent and Z is the volume of said sample solution, is known and is greater than 1; said method comprising
   (1) determining a ratio equal to said measured spectophotometric property of said reference solution divided by said measured spectrophotometric property of said further diluted sample solution, said properties corrected for said specrophotometric property of said blank solution,
   (2) determining a factor equal to said calculated concentration of said reference solution divided by said calculated concentration of said sample solution and multiplied by said term, wherein said solubility is equal to
      (a) said calculated concentration of said reference solution divided by said ratio and multiplied by said term when said ratio is greater than said factor,
      (b) or is greater than said calculated concentration of said sample solution when said ratio is equal to said factor.

8. The method of claim 7 wherein said cosolvent is selected from the group consisting of acetonitrile, methanol, ethanol, iso-propanol, 1-propanol, 1,4-dioxane, dimethylformamide, acetone, ethylene glycol, propylene glycol, polyethylene glycol 400, tetrahydrofuran, DMSO and mixtures thereof.

9. The method of claim 8, wherein said cosolvent is 1-propanol.

10. The method of claim 9, wherein:
a. said blank is prepared by diluting 1 aliquot of said buffer with 1 aliquot of said cosolvent,
b. said reference solution is prepared by diluting 1 aliquot of stock solution with 19 aliquots of DMSO; and 1 aliquot of said diluted solution is further diluted by 15 aliquots of said buffer and 15 aliquots of said cosolvent;
c. said sample solution is prepared by diluting 1 aliquot of stock solution with 400 aliquots of said buffer, allowing said sample solution to equilibrate for several hours, after which said sample solution is separated from any precipitate; and 1 aliquot of said sample solution is further diluted by 1 aliquot of cosolvent, wherein said term is equal to 2; said method comprising determining said ratio, wherein said solubility is equal to
   (1) said calculated concentration of said reference solution divided by said ratio and multiplied by 2 when said ratio is greater than said factor,
   (2) or is greater than said calculated concentration of said sample solution when said ratio is equal to said factor.

11. The method of claim 1 wherein said spectrophotometric property is determined at more than one wavelength, and the values at said wavelengths are corrected to account for the presence of interferences, said corrections being based on
a. comparing the shape of the spectrophotometric property—wavelength curve measured for said reference solution to the shape of said curve measured for said sample solution, and
b. applying weighting factors, wherein those portions of said curve associated with said sample solution that differ from the corresponding curve associated with said reference solution contribute less to said method than those where said shapes are similar.

12. The method of claim 1, wherein said buffer provides constant buffering capacity over the range of pH 3–10 and has low-UV absorbance.

13. Method of claim 12, wherein
a. said buffer is titrated with a standardized strong acid or strong base titrant solution in the pH interval 3–10;
b. said titration procedure produces a titration curve, linearly relating volumes of titrant to pH values;
c. said titration curve is used to calculate the appropriate volume of said titrant to add to said sample, said reference, and said blank solutions made with said buffer, to establish the pH values of the solutions, without actually having to measure the pH values of the solutions using a conventional pH electrode.

14. The method for high-throughput spectrophotometric measurement of the aqueous solubility of a compound, said compound having limited solubility in an aqueous buffer, not requiring knowledge or measurement of the molar absorptivity of said compound, and not requiring a calibration curve relating known concentrations of said compound to spectrophotometric properties of said compound, comprising:
a. preparing a sample solution of said compound in an aqueous buffer of known pH, and separating said sample solution from any precipitate,
b. preparing a reference solution that has a known concentration of said compound in said buffer, under conditions avoiding or suppressing precipitation,
c. preparing a blank solution free of said compound, but otherwise of the same composition as said reference solution,
d. measuring a spectrophotometric property of said sample, reference, and blank solutions, with or without further dilution thereof with cosolvent, wherein said cosolvent possesses one or more of the properties selected from the group consisting of (1) high capacity to dissolve said compound, (2) low UV absorption, and (3) low vapor pressure, and
e. determining the concentration of the sample solution by comparing the measured spectrophotometric property of said sample, reference and blank solutions, and calculating from said determination the solubility of said compound if said sample solution constitutes a saturated solution, wherein
   said compound is ionizable and anomalies are present in solution,
   several measurements of said aqueous solubility are made, each at a different known value of pH, and the intrinsic aqueous solubility is determined, said method comprising
   i. plotting the logarithm of the aqueous solubility of said compound against pH to produce a logarithm aqueous solubility-pH curve, ii. obtaining the apparent $pK_a$ of said compound in said solution having said anomaly by locating the pH value at the intersection of the horizontal asymptote indicating the logarithm of the apparent intrinsic solubility and the diagonal asymptote of said logarithm aqueous solubility-pH curve, iii. independently obtaining the $pK_a$ of said compound in aqueous solution free of said anomaly and determining the apparent shift of the $pK_a$ caused by said anomaly, and iv. using said apparent shift of the $pK_a$ to remove the effect of the anomaly and determine the intrinsic aqueous solubility of said compound.

15. The method of claim 14, wherein said anomaly is caused by one or more factors selected from the group consisting of:

a. self-association effects, b. presence of bile acids or other surfactants, c. presence of cyclodextrins, d. presence of ion-pair forming counterions, e. presence of non-ionizable polymers, f. presence of phospholipids, and g. presence of DMSO.

16. The method of claim 15, wherein said anomaly is caused by the presence of DMSO, and said $pK_a$ of said compound in butter free of anomaly is determined by using known analytical techniques, said method comprising a. determining the apparent $pK_a$ of said compound in said solution having said anomaly by locating on said logarithm aqueous solubility-pH curve the pH value at the intersection of the horizontal asymptote indicating the apparent aqueous intrinsic solubility and the diagonal asymptote of said curve, b. determining the difference between (1) said apparent $pK_a$ of said compound in said solution having said anomaly and (2) the $pK_a$ of said compound in aqueous solution free of anomaly, and c. provided that, (1) for ionizable acids, said difference is greater than zero, or (2) for ionizable bases, said difference is less than zero, subtracting or adding for ionizable acids or bases, respectively, said difference to the logarithm of said apparent intrinsic solubility to determine the logarithm of the intrinsic aqueous solubility of said compound in said buffer free of said anomaly.

17. The method of claim 14 wherein said spectrophotometric property is determined at more than one wavelength, and the values at said wavelengths are corrected to account for the presence of interferences, said corrections being based on a. comparing the shape of the spectrophotometric property—wavelength curve measured for said reference solution to the shape of said curve measured for said sample solution, and b. applying weighting factors, wherein those portions of said curve associated with said sample solution that differ from the corresponding curve associated with said reference solution contribute less to said method than those where said shapes are similar.

18. The method of claim 17 wherein said spectrophotometric property is UV absorbance and said interferences are spurious spectrophotometric anomalies due to impurities, dust, or air bubbles.

19. The method of claim 14, wherein said buffer provides constant buffering capacity over the range of pH 3–10 and has low-UV absorbance.

20. The method of claim 19 wherein said buffer comprises acetic acid, MES, HEPES and boric acid dissolved in water, with concentrations selected to ensure constant buffer capacity.

21. The method of claim 19, wherein said buffer comprises glycolic acid, MES, HEPES, and taurine, dissolved in a mixture of water and acetonitrile, with concentrations selected to ensure constant buffer capacity.

* * * * *

UNITED STATES PATENT AND TRADEMARK OFFICE
CERTIFICATE OF CORRECTION

PATENT NO. : 6,569,686 B2
DATED : May 27, 2003
INVENTOR(S) : Alex Avdeef et al.

It is certified that error appears in the above-identified patent and that said Letters Patent is hereby corrected as shown below:

Column 1,
Lines 31 and 33, "i Pharm. Res." should read -- *Pharm. Res.* --;
Line 32, "i Pharm Pharmacol." should read -- *Pharm. Pharmacol.* --;

Column 14,
Line 44, "$a_{max}^{REF}F$," should read -- $a_{max}^{REF}$, --;

Column 29,
Line 5, "butter" should read -- buffer --;

Column 30,
Line 27, "The" should read -- A --;
Line 54, "the solubility" should read -- the aqueous solubility --; and Column 31,
Line 26, "butter" should read -- buffer --.

Signed and Sealed this

Twenty-second Day of March, 2005

JON W. DUDAS
*Director of the United States Patent and Trademark Office*